(12) United States Patent
Marchitto et al.

(10) Patent No.: US 6,387,059 B1
(45) Date of Patent: May 14, 2002

(54) INTERSTITIAL FLUID MONITORING

(75) Inventors: Kevin S. Marchitto; Stephen T. Flock, both of Little Rock, AR (US)

(73) Assignee: Transmedica International, Inc., Victoria (AU)

( * ) Notice: Subject to any disclaimer, the term of this patent is extended or adjusted under 35 U.S.C. 154(b) by 0 days.

(21) Appl. No.: 09/443,782

(22) Filed: Nov. 19, 1999

Related U.S. Application Data

(63) Continuation of application No. 08/955,982, filed on Oct. 22, 1997, now Pat. No. 6,056,738, which is a continuation of application No. 08/792,335, filed on Jan. 31, 1997, now abandoned, which is a continuation of application No. 08/126,241, filed on Sep. 24, 1993, now Pat. No. 5,643,252.

(51) Int. Cl.$^7$ .......................... A61B 10/00; A61B 18/18
(52) U.S. Cl. .............................. 600/573; 606/9; 606/2; 128/898
(58) Field of Search ........................... 606/9, 300, 310, 606/309, 573; 604/20, 49; 128/897, 720

(56) References Cited

U.S. PATENT DOCUMENTS

| | | |
|---|---|---|
| 3,865,113 A | 2/1975 | Sharon et al. |
| 4,028,636 A | 6/1977 | Hughes |
| 4,628,416 A | 12/1986 | Dewey |

(List continued on next page.)

FOREIGN PATENT DOCUMENTS

| | | |
|---|---|---|
| EP | 0214712 A1 | 3/1987 |
| JP | 4-314428 | 11/1992 |
| JP | 7-39542 | 2/1995 |
| RU | 2005515 | 1/1994 |
| RU | 2027450 | 1/1995 |
| SU | 1614808 | 3/1988 |
| SU | 1670858 | 10/1989 |
| WO | WO92/14514 | 9/1992 |
| WO | WO94/09713 | 5/1994 |
| WO | WO97/07734 | 3/1997 |

OTHER PUBLICATIONS

Nelson et al., Mid Infrared Laser Ablation of Stratum Corneum Enhances In Vitro Percutaneous Transport of Drugs, The Society for investigative Dermatology, Inc., p. 874–879, Sep. 10, 1990.*

"Laser Scrifier" advertisement in Russian, published Nov. 19, 1990; translation into English provided.

Jacques et al. "Controlled Removal of Human Stratum Corneum by Pulsed Laser," The Journal of Investigative Dermatology, vol. 88, No. 1, Jan., 1987; pp. 88–93.

N. Ito et al., "Development Of A Transcutaneous Blood–Constituent Monitoring Method Using A Suction Effusion Fluid Collection Technique And An Ion–Sensitive Field–Effect Transistor Glucose Sensor" Medical & Biological Engineering & Computing, vol. 32, No. 3, May 1994, pp. 242–246.

(List continued on next page.)

*Primary Examiner*—Eric F. Winakur
*Assistant Examiner*—Michael Astorino
(74) *Attorney, Agent, or Firm*—Irell & Manella LLP

(57) ABSTRACT

The present invention provides an improved method of measuring analytes in bodily fluids without the use of a sharp. The method having the steps of irradiating the skin of a patient by focused pulses of electromagnetic energy emitted by a laser. By proper selection of wavelength, energy fluence, pulse temporal width and irradiation spot size, the pulses precisely irradiate the skin to a selectable depth, without causing clinically relevant damage to healthy portions of the skin. After irradiation, interstitial fluid is collected into a container or left on the skin. The interstitial fluid is then tested for a desired analyte to approximate the analyte concentration in other bodily fluids. Alternatively, after the forced formation of a microblister, the epidermis covering the microblister is lysed and the interstitial fluid is subsequently collected and tested.

26 Claims, 28 Drawing Sheets

U.S. PATENT DOCUMENTS

| | | | |
|---|---|---|---|
| 4,648,892 A | | 3/1987 | Kittrell et al. |
| 4,710,940 A | | 12/1987 | Sipes, Jr. |
| 4,712,537 A | | 12/1987 | Pender |
| 4,775,361 A | | 10/1988 | Jacques |
| 4,829,262 A | | 5/1989 | Furumoto |
| 4,882,492 A | | 11/1989 | Schlager |
| 4,940,411 A | | 7/1990 | Vassiliadis et al. |
| 4,941,093 A | | 7/1990 | Marshali et al. |
| 4,951,663 A | | 8/1990 | L'Esperance, Jr. |
| 4,960,467 A | | 10/1990 | Peck |
| 5,066,291 A | | 11/1991 | Stewart |
| 5,066,293 A | | 11/1991 | Furumoto |
| 5,074,861 A | | 12/1991 | Schneider et al. |
| 5,125,922 A | | 6/1992 | Dwyer et al. |
| 5,165,418 A | * | 11/1992 | Tankovich ..................... 606/9 |
| 5,182,759 A | | 1/1993 | Anthon et al. |
| 5,231,975 A | | 8/1993 | Bommanan et al. |
| 5,290,273 A | | 3/1994 | Tan |
| 5,304,170 A | | 4/1994 | Green |
| 5,312,395 A | | 5/1994 | Tan et al. |
| 5,342,355 A | | 8/1994 | Long |
| 5,360,426 A | | 11/1994 | Muller et al. |
| 5,360,447 A | | 11/1994 | Koop |
| 5,397,327 A | | 3/1995 | Koop et al. |
| 5,421,816 A | | 6/1995 | Lipkovker |
| 5,423,798 A | | 6/1995 | Crow |
| 5,423,803 A | | 6/1995 | Tankovich et al. |
| 5,437,658 A | | 8/1995 | Muller et al. |
| 5,445,611 A | | 8/1995 | Eppstein et al. |
| 5,458,140 A | | 10/1995 | Eppstein et al. |
| 5,461,212 A | | 10/1995 | Seiler et al. |
| 5,468,239 A | | 11/1995 | Tanner et al. |
| 5,522,813 A | | 6/1996 | Trelles |
| 5,554,153 A | * | 9/1996 | Costello et al. ................. 606/9 |
| 5,582,184 A | | 12/1996 | Erickson et al. |
| 5,586,981 A | | 12/1996 | Hu |
| 5,611,795 A | | 3/1997 | Slatkine et al. |
| 5,614,502 A | | 3/1997 | Flotte et al. |
| 5,617,851 A | | 4/1997 | Lipkovker |
| 5,624,434 A | | 4/1997 | Abergel et al. |
| 5,630,811 A | | 5/1997 | Miller |
| 5,636,632 A | | 6/1997 | Bommannan et al. |
| 5,642,370 A | | 6/1997 | Mitchell et al. |
| 5,643,252 A | | 7/1997 | Waner et al. |
| 5,644,585 A | | 7/1997 | Mitchell et al. |
| 5,658,892 A | | 8/1997 | Flotte et al. |
| 5,713,845 A | * | 2/1998 | Tankovich ..................... 606/9 |

OTHER PUBLICATIONS

D. Christensen et al., "Evanescent Coupling In A Waveguide Fluoroimmunosensor" Progress in biomedical Optics–Proceeding of Fiber Optice Medical And Fluorescent Sensors and Applications, vol. 1648 Jan. 23–24 1992.

J. De Boer et al. "Application of Transcutaneous Microdialysis and Continuous Flow Analysis for On–line Glucose Monitoring in Newborn Infants" The Journal of Laboratory and Clinical Medicine, vol. 124, No. 2, Aug. 1994, pp. 210–217.

G. Rao et al., "Reverse Iontophoresis: Development of a Noninvasive Approach for Glucose Monitoring" Pharmaceutical Research, Dec. 1993 vol. 10, No. 12 pp. 1751–1755.

R. O. Esenaliev et al. "Effect of Tensile Stress Amplitude and Temporl Characteristics on Threshold of Cativation–Driven Ablation" SPIE vol. 2681 Jul. 1996 pp. 326–333.

S. L. Jacques et al. "Laser–flash Photography of Laser–induced Spallation in Liquid Media"SPIE vol. 1646, May 1992, pp. 284–294.

S. Flock et al., "Photoacoustic–induced Vascular Tissue Dissection Resulting from Irradiation with a Q–Switched Frequency–doubled Nd:YAG Laser" SPIE vol. 2395, Apr. 1995, pp. 170–176.

D. Stern et al. "Corneal Ablation by Nanosecond, Picosecond, and Femtosecond Lasers at 532 and 625 nm" Archives of Ophthalmology Apr. 1989, vol. 107–American Medical Association, pp. 587–592.

L. Esterowitz, C. A. Hoffman, K. Levin and M. Storm, "Mid–IR Solid State Laser with Fiber Optics as an Ideal Medical Scalpel," In Proceedings Intern. Conference on Lasers, Las Vegas, 1985, pp. 68–71.

Al Krogstad et al., "Microdialysis Methodology for the Measurement of Dermal Interstitial Fluid in Humans," Br J Dermatology, 134(6): 1005–12, Jun. 1996.

N. Ito et al., "Development of Non–Invasive Transcutaneous Blood Glucose Monitoring Method Using an ISFET Biosensor," Frontiers of Medical & Biological Engineering, 4(1):35–42, 1992.

Petersen et al., "Microdialysis of the Interstitial Water Space in Human Skin in Vivo: Quantitative Measurement of Cutaneous Glucose Concentrations," Journal of Investigative Dermatology, vol. 3, 357–360, Sep. 1992.

F. Sternberg et al., "Subcutaneous Glucose Concentration in Humans," Diabetes Care, vol. 18, 1266–1269, Sep. 1995.

F. Schmidt et al., "Glucose Concentrations in Subcutaneous Extracellular Space," Diabetes Care, vol. 16, 695–700, May 1993.

* cited by examiner

F.G. 7B

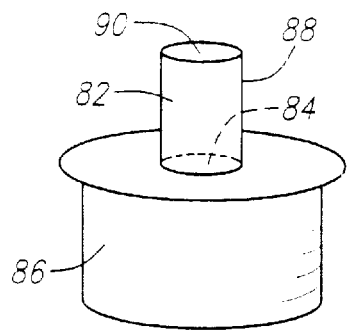
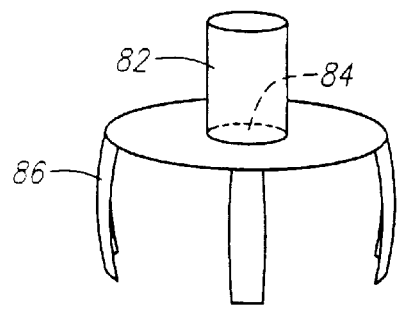
FIG. 17A                FIG. 17B
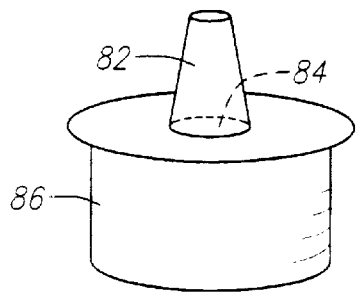
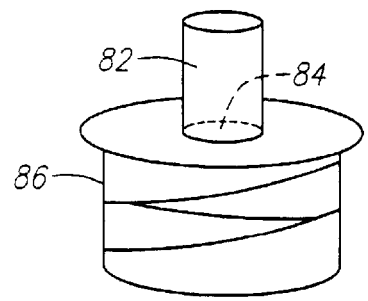
FIG. 17C                FIG. 17D
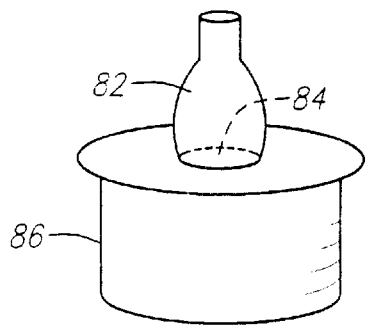
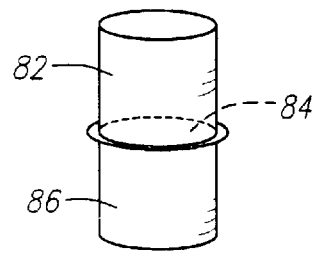
FIG. 17E                FIG. 17F
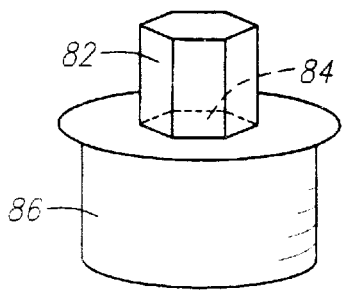
FIG. 17G

50 mJ Er:YAG LASER IRRADIATION HUMAN SKIN

80 mJ Er:YAG LASER IRRADIATION HUMAN SKIN

READINGS ARE DIFFERENCES FROM SEPARATE CONTROLS ON CONTRALATERAL ARM

INTERSTITIAL FLUID MONITORING

This application is a continuation of application Ser. No. 08/955,982. filed Oct. 22, 1997, issued May 2, 2000 as U.S. Pat. No. 6,056,738, which is a continuation-in-part of U.S. Ser. No. 08/792,335, filed Jan. 31, 1997, now abandoned, which is a continuation-in-part of U.S. Ser. No. 08/126,241, filed Sept. 24, 1993, issued Jul. 1, 1997 as U.S. Pat. No. 5,643,252, all of which are incorporated herein by reference.

FIELD OF THE INVENTION

This invention is in the field of medical procedures, namely laser medical equipment used to perforate or alter tissue for monitoring analyte concentration in bodily fluids.

BACKGROUND

The traditional method of measuring blood glucose, or other analytes, consists of taking a blood sample and then measuring the analyte concentration in the blood or plasma. The blood is typically collected from a patient utilizing mechanical perforation of the skin with a sharp device such as a metal lancet or needle.

This procedure has many drawbacks, including the possible infection of health care workers and the public by the sharp device used to perforate the skin, as well as the cost of handling and disposal of biologically hazardous waste.

When skin is perforated with a sharp device such as a metal lancet or needle, biological waste is created in the form of the "sharp" contaminated by the patient's blood and/or tissue. If the patient is infected with blood-born agents, such as human immunodeficiency virus (HIV), hepatitis virus, or the etiological agent of any other diseases, the contaminated sharp poses a serious threat to others that might come in contact with it. For example, many medical workers have contracted HIV as a result of accidental contact with a contaminated sharp.

Post-use disposal of contaminated sharps imposes both logistical and financial burdens on the end user. These costs are imposed as a result of the social consequences of improper disposal. For example, in the 1980's improperly disposed biological wastes washed up on public beaches on numerous occasions. Improper disposal also permits others, such as intravenous drug users, to obtain contaminated needles and spread disease.

There exists an additional drawback of the traditional method of using a needle for drawing fluids. The pain associated with being stabbed by a the sharp instrument can be a traumatizing procedure, especially in pediatric patients, causing significant stress and anxiety in the patient. Moreover, the stabbing procedure often must be repeated before sufficient fluid is obtained. For analytes that need to be constantly monitored, patients may not comply with the frequency of measurement due to the pain involved. In the case of diabetics, failure to measure glucose levels can result in a life-threatening situation.

In addition to blood withdrawal, concentrations of analytes in interstitial fluid can be measured for accurate representation of analyte concentration in the blood. Because of the strong barrier properties of the stratum corneum, however, collecting interstitial fluid through the stratum corneum poses problems. To reduce the barrier function of the stratum corneum, a number of different techniques are presently used, these include: (1) using a metal lancet to cut the skin, (2) chemical enhancers, (3) ultrasound, (4) tape stripping, and (5) iontophoresis. Chemical enhancers pose the problem of potentially reacting with the analyte to be measured. Moreover, the time lapse after application to propagation of interstitial fluid is great. Tape stripping is unsatisfactory because of the pain to the patient. Iontophoresis and ultrasound, similarly have drawbacks in the collection time and the quantity of fluid removed. As previously discussed, the use of a metal lancet has the drawback of patient discomfort and the possibility of contamination.

Thus, a need exists for a method to easily measure the constituents in the blood or other bodily fluids, without: (1) the use of a sharp object, (2) the slow speed of fluid collection, or (3) the pain currently associated with the elimination or reduction of the barrier function of the stratum corneum. The method would further obviate the need for disposal of contaminated sharps and eliminate the pain associated with sharp instruments. The desired method would also, ideally, increase patient compliance for monitoring the desired analyte. The method and apparatus disclosed herein achieves these and other goals.

Lasers have been used in recent years as a very efficient precise tool in a variety of surgical procedures. Among potentially new sources of laser radiation, the rare-earth elements are of major interest for medicine. One of most promising of these is a YAG (yttrium, aluminum, garnet) crystal doped with erbium (Er) ions. With the use of this crystal, it is possible to build an erbium-YAG (Er:YAG) laser which can be configured to emit electromagnetic energy at a wavelength (2.94 microns), among other things, which is strongly absorbed by water. When tissue, which consists mostly of water, is irradiated with radiation at or near this wavelength, energy is transferred to the tissue. If the intensity of the radiation is sufficient, rapid heating can result followed by vaporization of tissue can result. In addition, or alternatively, deposition of this energy can result in photomechanical disruption of tissue. Some medical uses of Er:YAG lasers have been described in the health-care disciplines of dentistry, gynecology and ophthalmology. See, e.g., Bogdasarov, B. V., et al., "The Effect of Er: YAG Laser Radiation on Solid and Soft Tissues", Preprint 266, Institute of General Physics, Moscow, 1987; Bol'shakov, E. N. et al., "Experimental Grounds for Er:YAG Laser Application to Dentistry", SPIE 1353:160–169, Lasers and Medicine (1989) (these and all other references cited herein are expressly incorporated by reference as if fully set forth in their entirety herein). Laser perforators of the type explained in U.S. Pat. No. 5,643,252, said patent being incorporated by reference herein, have generally been designed to perforate or alter the tissue of a patient to reduce the barrier function of the stratum corneum, thus allowing for transport of fluid through the target tissue.

SUMMARY OF THE INVENTION

The present invention employs a laser to perforate or alter the skin of a patient for removal and subsequent analysis of interstitial fluid. These measurements can then be used to approximate analyte concentrations in other bodily fluids, such as blood. Prior to application, the care giver properly selects the wavelength, energy fluence (energy of the pulse divided by the area irradiated), pulse temporal width and irradiation spot size so as to precisely perforate or alter the target tissue to a select depth and eliminate undesired damage to healthy proximal tissue. After perforation or alteration, interstitial fluid is allowed to propagate to the surface of the skin for collection and testing.

According to one embodiment of the present invention, a laser emits a pulsed laser beam, focused to a small spot for the purpose of perforating or altering the target tissue. By adjusting the output of the laser, the laser operator can control the depth, width and length of the perforation or alteration as needed, such as to avoid drawing blood into the interstitial fluid sample.

In another embodiment, continuous-wave or diode lasers may be used to duplicate the effect of a pulsed laser beam. These lasers are modulated by gating their output, or, in the case of a diode laser, by fluctuating the laser excitation current. The overall effect is to achieve brief irradiation, or a series of brief irradiations, that produce the same tissue permeating effect as a pulsed laser.

The term "perforation" is used herein to indicate the ablation of the stratum corneum to reduce or eliminate its barrier function. The term "alteration" of the stratum corneum is used herein to indicate a change in the stratum corneum which reduces or eliminates the barrier function of the stratum corneum and increases permeability without ablating, or by merely partially ablating, the stratum corneum itself. A pulse or pulses of infrared laser radiation at a subablative energy of, e.g., 60 mJ using a TRANSMEDICA™ International, Inc. ("TRANSMEDICA™") Er:YAG laser (see U.S. Pat. No. 5,643,252, Waner et al., which is incorporated herein by reference) with a beam of radiant energy with a wavelength of 2.94 microns, a 200 μs (microsecond) pulse, and a 2 mm spot size) will alter the stratum corneum. The technique may be used for transdermal drug delivery or for obtaining fluid samples from the body. Different wavelengths of laser radiation and energy levels less than or greater than 60 mJ may also produce the enhanced permeability effects without ablating the skin.

The mechanism for this alteration of the stratum corneum is not certain. It may involve changes in lipid or protein nature or function or be due to desiccation of the skin or mechanical alterations secondary for propagating pressure waves or cavitation bubbles. The pathway that topically applied drugs take through the stratum corneum is generally thought to be through cells and/or around them, as well as through hair follicles. The impermeability of skin to topically applied drugs is dependent on tight cell to cell junctions, as well as the biomolecular makeup of the cell membranes and the intercellular milieu. Any changes to either the molecules that make up the cell membranes or intercellular milieu, or changes to the mechanical structural integrity of the stratum corneum and/or hair follicles can result in reduced barrier function. It is believed that irradiation of the skin with radiant energy produced by the Er:YAG laser causes measurable changes in the thermal properties, as evidenced by changes in the Differential Scanning Calorimeter (DSC spectra as well as the Fourier Transform Infrared (FTIR) spectra of stratum corneum. Changes in DSC and FTIR spectra occur as a consequence of changes in molecules or macromolecular structure, or the environment around these molecules or structures. Without wishing to be bound to any particular theory, we can tentatively attribute these observations to changes in lipids, water and protein molecules in the stratum corneum caused by irradiation of molecules with electromagnetic radiation, both by directly changing molecules as well as by the production of heat and pressure waves which can also change molecules.

Both perforation and alteration change the permeability parameters of the skin in a manner which allows for increased passage of body fluids or pharmaceuticals across the stratum corneum.

The term "lyse" is used herein to indicate the breaking up of the epidermis layer covering a microblister. The energy pulse used to accomplish this is between the energy required for ablation and sub-ablation.

Accordingly, one object of the present invention is to provide a means for perforating or altering the stratum corneum of a patient in a manner that does not result in bleeding. For example, the perforation or alteration created at the target tissue is accomplished by applying a laser beam that penetrates through the stratum corneum layer or both the stratum corneum layer and the epidermis, thereby reducing or eliminating the barrier function of the stratum corneum. This procedure allows for the subsequent removal of fluids, specifically interstitial fluid, through the skin.

Another object of this invention is to draw interstitial fluid through the perforation or alteration site (or allowing the interstitial to propagate on its own to the surface of the skin). The interstitial fluid can then be collected.

In a preferred embodiment, by selection of appropriate wavelength, energy fluence, pulse temporal width and irradiation spot size, the skin tissue is perforated deep into the epidermis. After perforation, interstitial fluid is collected into an awaiting container.

In a further preferred embodiment, by selection of appropriate wavelength, energy fluence, pulse temporal width and irradiation spot size, just the stratum corneum is perforated or altered and the interstitial fluid is then allowed to propagate to surface. The fluid is then collected into a container unit for testing, or the fluid is left on the skin surface for subsequent testing.

In an additional preferred embodiment, before perforation or alteration by the laser device, a blister, preferably a microblister, is created at the surface of the skin by subjecting the skin to sub-atmospheric pressure. This vacuum can be created by a separate device, or the vacuum system can be part of the laser perforator container unit. After the skin has been subjected to sub-atmospheric pressure (a pressure of slightly less than 1 atmosphere), a microblister is formed, whereby the epidermis is separated from the dermis. Interstitial fluid collects in this pocket and the laser perforator is then used to lyse the blister. After lysing, the interstitial fluid that formed inside the blister is collected into a container.

To further the speed in the collection of interstitial fluid, or to increase the delivery of pharmaceuticals into the body, pressure gradients in the tissue can be created. In this embodiment, pressure gradients are created using short rapid pulses of radiant energy on the tissue. This pressure gradient can be used to force substances, such as interstitial fluid, out of the body, or to transfer a substance into the body, through a perforation or alteration site. In another embodiment of this invention, pressure waves, plasma, and cavitation bubbles are created in or above the stratum corneum to increase the permeation of the compounds (e.g., pharmaceuticals) or fluid, gas or other biomolecule removal. This method may simply overcome the barrier function of intact stratum corneum without significant alteration or may be used to increase permeation or collection in ablated or altered stratum corneum. Additionally, to increase diffusion, plasma can be produced by irradiating the surface of the target tissue, or material on the target tissue, with a pulse or pulses of electromagnetic energy from a laser. Prior to treatment, the care giver properly selects the wavelength, energy fluence (energy of the pulse divided by the area irradiated), pulse temporal width and irradiation spot size to create the plasma while limiting undesired damage to healthy proximal tissue. These technique for increasing the diffusion of fluids through the skin is not meant to limit the scope of this invention, but is merely an embodiment. Other techniques can be used, such as manual compression of the skin surrounding the perforation or alteration site, or the care giver can rely simply on the reduced barrier function of the perforation or alteration site for fluid to propagate to the skin surface.

In another embodiment, a typical laser is modified to include a container unit. Such a container unit can be added to: (1) increase the efficiency in the collection of fluids; (2) further testing of the collected sample, (3) apply a vacuum to the skin surface, (4) reduce the noise created when the laser beam perforates the patient's tissue; and (5) collect the ablated tissue. The optional container unit is alternatively evacuated to expedite the collection of the released materials, such as the fluids, or to expedite the blistering of the tissue. The container can also be used to collect only ablated tissue. The noise created from the laser beam's interaction with the patient's skin may cause the patient anxiety. The optional container unit reduces the noise intensity and therefore alleviates the patient's anxiety and stress. The container unit also minimizes the risk of cross-contamination and guarantees the sterility of the collected sample. The placement of the container unit in the use of this invention is unique in that it covers the tissue being irradiated, at the time of irradiation by the laser beam, and is therefore able to collect the fluid and/or ablated tissue as the perforation or alteration occurs.

An additional object of this invention is to allow the taking of measurements of various fluids constituents, such as glucose, collected through the perforation or alteration site. Typical testing techniques include infrared spectrometry, enzymatic analysis, electrochemical analysis and other means. The testing can be incorporated into the laser perforator device or the testing can be completed on the fluid after the container unit has been removed from the device. Additionally, testing can be completed on the surface of the skin, at the perforation or ablation site, after the interstitial fluid has propagated through the target tissue.

An additional object of this invention is to administer pharmaceuticals after measurement of the interstitial fluid. The appropriate drug dose can be delivered manually or automatically. Drug delivery can be triggered in combination with the monitoring of the desired analyte. For example, glucose measurements can be used to trigger the administration of insulin in diabetics.

A further object of this invention is to allow drugs to be administered continually on an outpatient basis over long periods of time. The speed and/or efficiency of drug delivery is thereby enhanced for drugs which were either slow or unable to penetrate skin.

A further object of this invention is to avoid the use of sharps. The absence of a contaminated sharp will eliminate the risk of accidental injury and its attendant risks to health care workers, patients, and others that may come into contact with the sharp. The absence of a sharp in turn obviates the need for disposal of biologically hazardous waste. Thus, the present invention provides an ecologically sound method for removing bodily fluids or administering pharmaceuticals.

A typical laser used for this invention requires no special skills to use (for example, the TRANSMEDICA™ Er:YAG laser). It can be small, lightweight and can be used with regular or rechargeable batteries. The greater the laser's portability and ease of use, the greater the utility of this invention in a variety of settings, such as a hospital room, clinic, or home.

Safety features can be incorporated into the laser that require that no special safety eyewear be worn by the operator of the laser, the patient, or anyone else in the vicinity of the laser when it is being used.

BRIEF DESCRIPTION OF THE DRAWINGS

The present invention may be better understood and its advantages appreciated by those skilled in the art by referring to the accompanying drawings wherein:

FIGS. 7A and 7B show alternative patches for sterilization and/or delivery of pharmaceutical.

FIGS. 17A–17G show various examples of a container unit.

DETAILED DESCRIPTION

Figure 1:
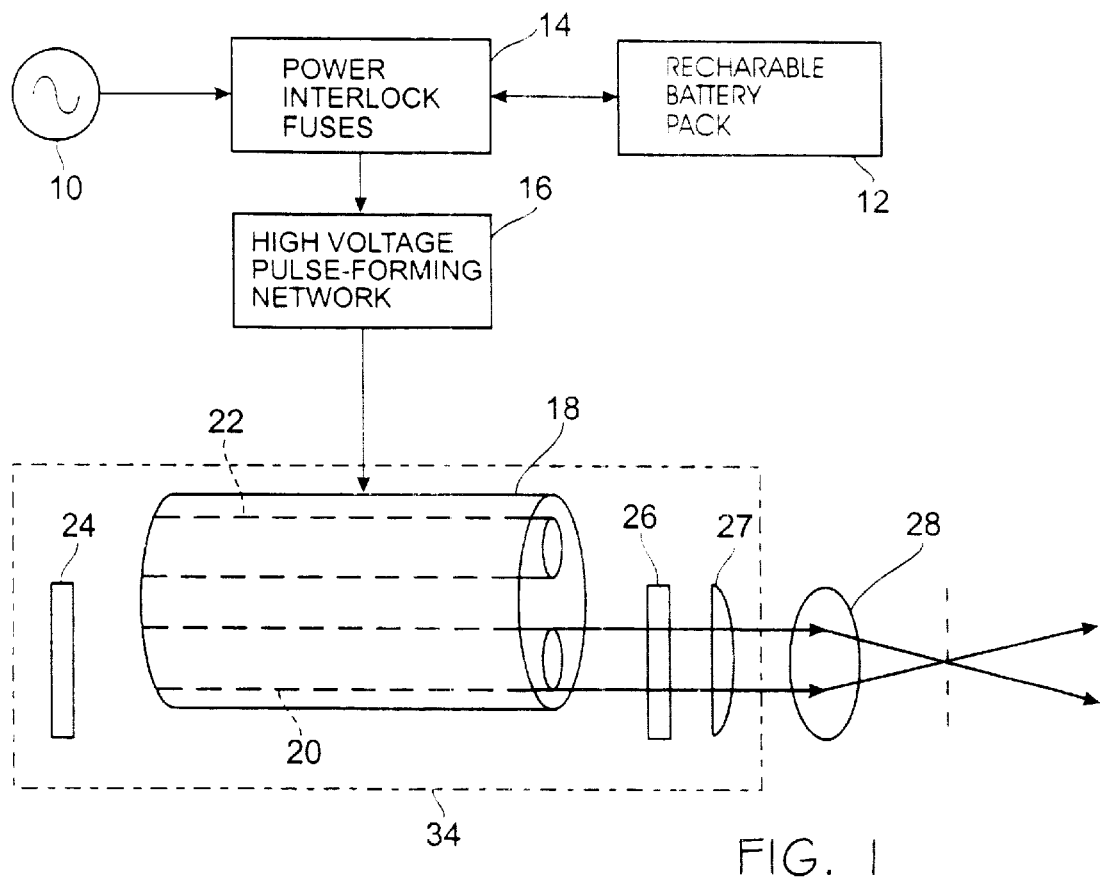
FIG. 1 shows a laser with its power source, high voltage pulse-forming network, flashlamp, lasing rod, mirrors, housing and focusing lens.

This invention provides a method for perforating or altering skin for the sampling and measurement of bodily fluids. The invention utilizes a laser beam, specifically focused, and lasing at an appropriate wavelength, to create small perforations or alterations in the skin of a patient. In a preferred embodiment, the laser beam has a wavelength between 0.2 and 10 microns. More preferably, the wavelength is between about 1.5 and 3.0 microns. Most preferably the wavelength is about 2.94 microns. In one embodiment, the laser beam is focused with a lens to produce an irradiation spot on the skin through the epidermis of the skin. In an additional embodiment, the laser beam is focused to create an irradiation spot only through the stratum corneum of the skin.

The caregiver may consider several factors in defining the laser beam, including wavelength, energy fluence, pulse temporal width and irradiation spot-size. In a preferred embodiment, the energy fluence is in the range of 0.03–100,000 $J/cm^2$. More preferably, the energy fluence is in the range of 0.03–9.6 $J/cm^2$. The beam wavelength is dependent in part on the laser material, such as Er:YAG. The pulse temporal width is a consequence of the purse width produced by, for example, a bank of capacitors, the flashlamp, and the laser rod material. The pulse width is optimally between 1 fs (femtosecond) and 1,000 $\mu$s.

According to the method of the present invention the perforation or alteration produced by the laser need not be produced with a single pulse from the laser. In a preferred embodiment the caregiver produces a perforation or alteration through the stratum corneum by using multiple laser pulses, each of which perforates or alters only a fraction of the target tissue thickness.

To this end, one can roughly estimate the energy required to perforate or alter the stratum corneum with multiple pulses by taking the energy in a single pulse, and dividing by the number of pulses desirable. For example, if a spot of a particular size requires 1 J of energy to produce a perforation or alteration through the entire stratum corneum, then one can produce qualitatively similar perforation or alteration using ten pulses, each having 1/10th the energy. Because it is desirable that the patient not move the target tissue during the irradiation (human reaction times are on the order of 100 ms or so), and that the heat produced during each pulse not significantly diffuse, in a preferred embodiment the pulse repetition rate from the laser should be such that complete perforation is produced in a time of less than 100 ms. Alternatively, the orientation of the target tissue and the laser can be mechanically fixed so that changes in the target location do not occur during the longer irradiation time.

To penetrate the skin in a manner which does not induce much if any blood flow, skin is perforated or altered through the outer surface, such as the stratum corneum layer, but not as deep as the capillary layer. The laser beam is focussed precisely on the skin, creating a beam diameter at the skin in the range of approximately 0.5 microns–5.0 cm. Optionally, the spot can be slit-shaped, with a width of about 0.05–0.5 mm and a length of up to 2.5 mm. The width can be of any size, being controlled by the anatomy of the area irradiated and the desired permeation rate of the fluid to be removed or the pharmaceutical to be applied. The focal length of the focusing lens can be of any length, but in one embodiment it is 30 mm.

By modifying wavelength, pulse length, energy fluence (which is a function of the laser energy output (in Joules) and size of the beam at the focal point ($cm^2$)), and irradiation spot size, it is possible to vary the effect on the stratum corneum between ablation (perforation) and non-ablation or partial alteration (alteration). Both ablation and non-ablative alteration of the stratum corneum result in enhanced permeation of bodily fluids or subsequently applied pharmaceuticals.

For example, by reducing the pulse energy while holding other variables constant, it is possible to change between ablative and non-ablative tissue-effect. Using the TRANS-MEDICA™ Er:YAG laser, which has a pulse length of about 300 $\mu$s, with a single pulse or radiant energy and irradiating a 2 mm spot on the skin, a pulse energy above approximately 100 mJ causes partial or complete ablation, while any pulse energy below approximately 100 mJ causes partial ablation or non-ablative alteration to the stratum corneum. Optionally, by using multiple pulses, the threshold pulse energy required to enhance permeation of bodily fluids or for pharmaceutical delivery is reduced by a factor approximately equal to the number of pulses.

Alternatively, by reducing the spot size while holding other variables constant, it is also possible to change between ablative and non-ablative tissue-effect. For example, halving the spot area will result in halving the energy required to produce the same effect. Irradiations down to 0.5 microns can be obtained, for example, by coupling the radiant output of the laser into the objective lens of a microscope objective. (e.g., as available from Nikon, Inc., Melville, N.Y.). In such a case, it is possible to focus the beam down to spots on the order of the limit of resolution of the microscope, which is perhaps on the order of about 0.5 microns. In fact, if the beam profile is Gaussian, the size of the affected irradiated area can be less than the measured beam size and can exceed the imaging resolution of the microscope. To non-ablatively alter tissue in this case, it would be suitable to use a 3.2 J/cm$^2$ energy fluence, which for a half-micron spot size, would require a pulse energy of about 5 nJ. This low a pulse energy is readily available from diode lasers, and can also be obtained from, for example, the Er:YAG laser by attenuating the beam by an absorbing filter, such as glass.

Optionally, by changing the wavelength of radiant energy while holding the other variables constant, it is possible to change between an ablative and non-ablative tissue-effect. For example, using Ho:YAG (holmium: YAG; 2.127 microns) in place of the Er:YAG (erbium: YAG; 2.94 microns) laser, would result in less absorption of energy by the tissue, creating less of a perforation or alteration.

Picosecond and femtosecond pulses produced by lasers can also be used to produce alteration or ablation in skin. This can be accomplished with modulated diode or related microchip lasers, which deliver single pulses with temporal widths in the 1 femtosecond to 1 ms range. (See D. Stem et al., "Corneal Ablation by Nanosecond, Picosecond, and Femtosecond Lasers at 532 and 625 nm," Corneal Laser Ablation, vol. 107, pp. 587–592 (1989), incorporated herein by reference, which discloses the use of pulse lengths down to 1 femtosecond).

According to another object of this invention, after perforation or alteration of the target tissue, interstitial fluid is collected for subsequent measurement. To further collection of the fluid, different perforation or alteration depths can be created. In a preferred embodiment, the laser device perforates through the epidermis, allowing the interstitial fluid to propagate to the surface of the skin. In an additional preferred embodiment, perforation or alteration through the stratum corneum is completed, allowing the interstitial fluid to propagate to the surface of the skin, albeit more slowly.

Blistering to Enhance Collection of Interstitial Fluid

In a further embodiment, the laser perforator device is used in combination with sub-atmospheric pressure to obtain samples of interstitial fluid. By purposely applying a vacuum to the surface of the skin, it is possible to gently and reversibly separate the epidermis from the underlying dermis, thus creating a microblister in which interstitial fluid can collect.

The epidermis and dermis are interlocked by ridges and root like cytoplasmic microprocesses of basal cells that extend into the corresponding indentations of the dermis. This junction is further enforced by desmosomes which anchor the basal cells on the basal lamina, which is itself attached to the dermis by anchoring filaments and fibrils. In some cases, the hydrodynamic pressure of the plasma released by the superficial dermal blood vessels can lead to a lifting of the basal cells from the basal lamina thus leading to a (junctional) blister. Such a blister can be induced by suction, mild heat, certain compounds or liquid nitrogen. See Dermatology in General Medicine, 3d ed., T B Fitzpatrick, A Z Eisen, K. Wolff, I M Freedberg, and K F Austen, McGraw-Hill:NY (1987), incorporated herein by reference.

Low and Van der Leun ("Suction Blister Device for Separation of Viable Epidermis from Dermis", vol. 50, No. 2, pp. 308–314, Journal of Investigative Dermatology, 1968) describe the use of suction blisters, created in lower abdominal skin with reduced vacuum, for the purpose of obtaining interstitial fluid. They report that t=a/p, where a is a constant ($9 \times 10^8$ dyne/cm$^2$/sec) and p is the suction pressure. Thus, for example, a suction pressure of 200 mm Hg (760 mm Hg or $1.013 \times 10^6$ dyne/cm$^2$ is atmospheric pressure) will produce a blister in about 60 minutes. Van der Leun et al., (vol. 62, pp. 42–46, Journal of Investigative Dermatology, 1974), make the point that if skin temperature is raised (from 24 EC to 34 EC, for example), the time to the onset of the blister (for pressure of 410 mm Hg) is reduced from 30 to 7 minutes.

One embodiment of the present invention is to form a microblister by using negative pressure (slightly less than 1 atmosphere) applied to a small area on the skin. Subsequent lysing of the blister with the laser device produces a pathway through which the interstitial fluid can be collected. The vacuum acts to enhance the volume of interstitial fluid.

In another embodiment of the present invention, the vacuum means for drawing a microblister is incorporated into the lasing device. In an additional embodiment, the vacuum means is performed by an alternative device and the laser is then used to lyse the formed microblister.

In a further embodiment of the present invention, the vacuum is applied after ablation or alteration of the tissue, thereby propagating fluid through the lased site by negative pressure.

Pressure Wave to Enhance the Permeability of the Stratum Corneum or other Membranes In another embodiment of the present invention, a pressure gradient is created at the ablated or altered site to force substances through the skin. This technique can be used for the introduction of compounds including pharmaceuticals into the body or to remove fluids, gases or biomolecules from the body.

When laser radiant energy is absorbed by tissue, expansion (due to heating) and/or physical movement of tissue (due to heating or non-thermal effects such as spallation) takes place. These phenomena lead to production of propagating pressure waves, which can have frequencies in the acoustic (20 Hz to 20,000 Hz) or ultrasonic (>20,000 Hz) region of the pressure wave spectrum. For example, Flock et al. (Proc SPIE Vol. 2395, pp. 170–176, 1995) show that when a 20 ns pulse from a Q-switched frequency-doubled Nd:YAG laser is impacted on blood, propagating transient high pressure waves form. These pressure waves can be spectrally decomposed to show that they consist of a spectrum of frequencies, from about 0 to greater than 4 MHz. The high-pressure gradient associated with these kinds of compressional-type pressure waves can be transformed into tension-type or stress waves which can "tear" tissue apart in a process referred to as "spallation".

The absorption of propagating pressure waves by tissue is a function of the tissue type and frequency of wave.

Figure 44:
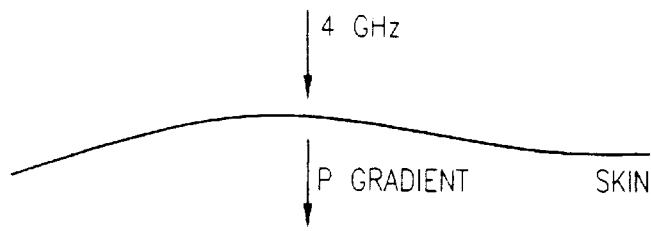
FIG. 44 shows a pressure gradient created in the stratum corneum.
Figure 47:
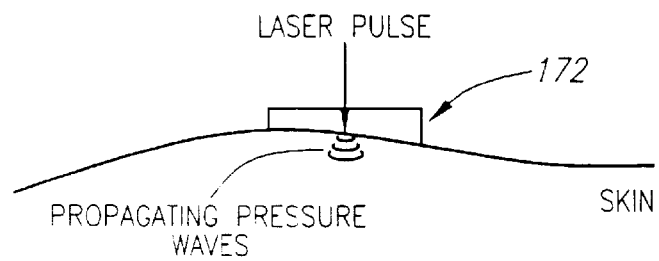
FIG. 47 shows a propagating pressure wave created at the skin surface with a transparent, or partially transparent, optic located on the skin.

Furthermore, the speed of these pressure waves in non-bone tissue is approximately 1400–1600 m/sec. Using these observations, a pressure gradient in tissue can be created, directed either into the body or out of the body, using pulsed laser radiant energy. To efficiently create pressure waves with a pulsed laser, the pulse duration needs to be less than the time it takes for the created heat to diffuse out of the region of interest. The effect is qualitatively equivalent to the effects of ultrasound on tissue. The attenuation coefficient for sound propagation in tissue increases approximately linearly with frequency (see, for example, J. Havlice and J. Taenzer, "Medical Ultrasound Imaging: An Overview of Principles and Instrumentation", Proc. IEEE 67, 620–641, 1979), and is approximately 1 dB/cm/MHz (note that a 20 decibel (dB) intensity difference is equivalent to a factor of 10 in relative intensity). The thickness of the stratum corneum is about 25 microns and the epidermis is about 200 microns. Thus, the frequency that is attenuated by 10 dB when propagating through the stratum corneum is 10 dB/(1 dB/cm/MHz*0.0025 cm), or 4 GHz. Similarly, as strongly absorbed radiant energy produced by a pulsed laser (say pulsed at 4 GHz) will produce propagating pressure waves of a similar frequency as the pulse repetition rate, it is possible to selectively increase the pressure in the stratum corneum or upper layers of skin as compared to the lower layers, thus enhancing the diffusive properties of topically applied drug (see, e.g., FIG. 44). A transparent, or nearly transparent, optic 172, as shown in FIG. 47, can be placed on the surface of the skin to contain the backward inertia of the propagating pressure wave or ablated stratum corneum.

Figure 45:
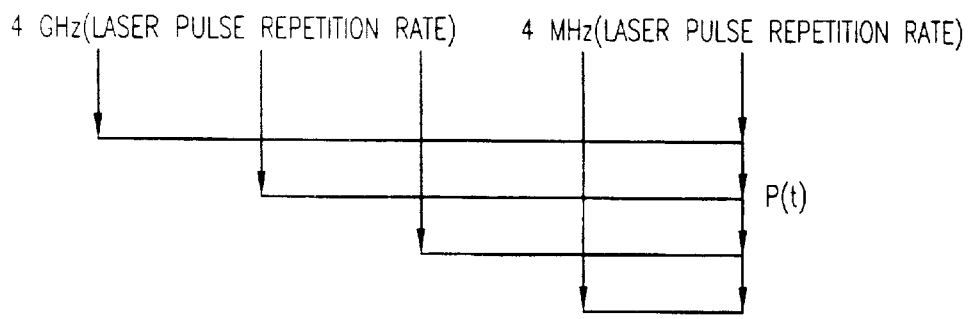
FIG. 45 is a schematic of modulating the pulse repetition frequency of radiant energy from high (4 GHz) to low (4 MHz).

In an additional embodiment, as shown in FIG. 45, by modulating the pulse repetition frequency of the radiant energy from high to low, it is possible to create transient pressure fields that can be designed to be beneficial for enhancing the diffusive properties of a topically applied pharmaceutical.

The high-frequency propagating pressure waves can also be produced from a single laser pulse. When tissue absorbs a brief pulse of laser irradiation, pressure waves with a spectrum of frequencies result. Some of these frequencies will propagate into lower layers in the skin, thus it may be possible to set up a reverse pressure gradient (more pressure below and less superficially) in order to enhance the diffusion of biomolecules out of the body effectively "pumping" them through the skin.

Acoustic waves and/or spallation are believed to occur during the use of the TRANSMEDICA™ Er:YAG laser in ablation of stratum corneum for drug delivery or perforation, since the 2.94 micron radiant energy is absorbed in about 1 micron of tissue, yet the tissue ablation can extend much deeper.

A continuous-wave laser can also be used to create pressure waves. A continuous-wave laser beam modulated at 5–30 MHz can produce 0.01–5 W/cm$^2$ pressure intensities in tissue due to expansion and compression of sequentially heated tissue (for example, a Q-switched Er:YAG laser (40 ns pulse) at 10 mJ and focussed to a spot size of 0.05 cm, with a pulse repetition rate of 5–30 MHz, would produce in stratum corneum a stress of about 3750 bars, or 0.025 W/cm$^2$). It takes a few hundred bars to cause transient permeability of cells. With this laser it requires about 0.01 W/cm$^2$ of continuous pressure wave energy to provide effective permeation of skin.

Figure 49:
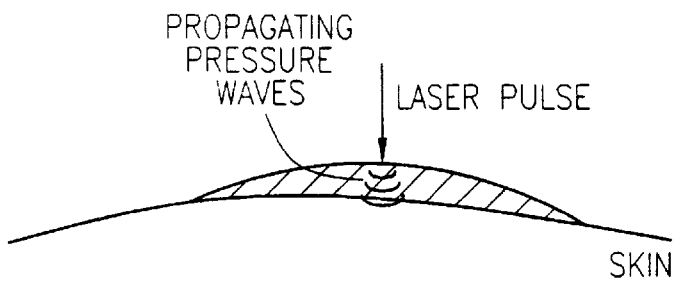
FIG. 49 shows a propagating pressure wave created in the applied pharmaceutical.

In an additional embodiment, pressure waves are induced on the topically applied pharmaceutical. The propagation of the wave towards the skin will carry some of the pharmaceutical with it (see, e.g., FIG. 49).

Figure 46:
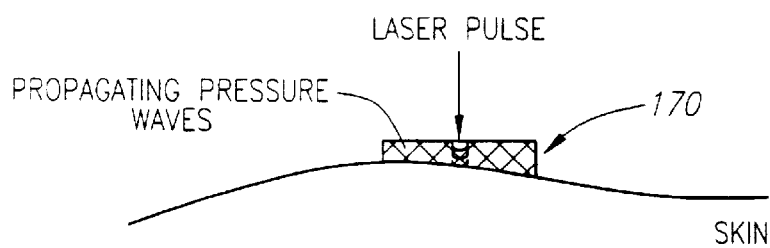
FIG. 46 shows a propagating pressure wave created in an absorbing material located on the skin.
Figure 48:
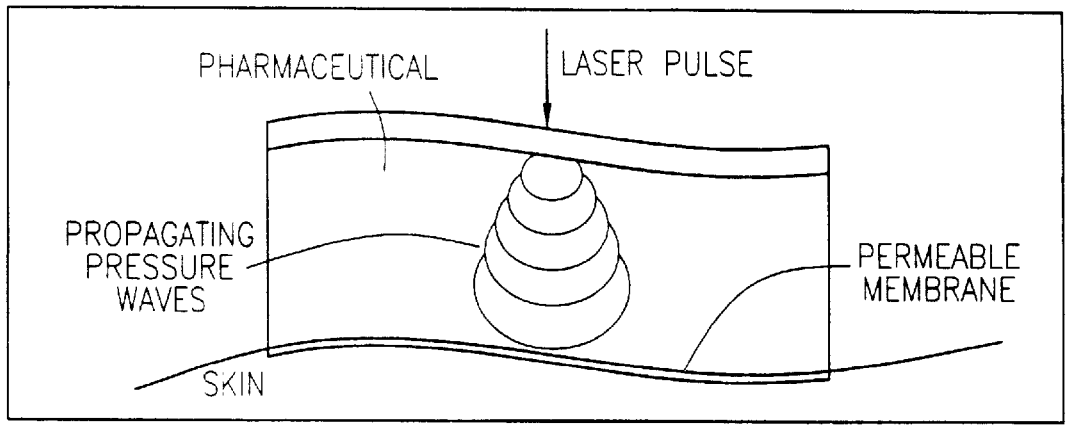
FIG. 48 shows a propagating pressure wave created in an absorbing material on the applied pharmaceutical.

In a further embodiment, pressure waves are induced on an absorbing material 170 placed over the topically applied pharmaceutical (see, e.g., FIG. 48). Preferably this material is a thin film of water, however, it can be created in any liquid, solid or gas located over the topically applied pharmaceutical. The propagation of the wave towards the skin will carry some of the pharmaceutical with it. Additionally, pressure waves can be induced on an absorbing material 170 (preferably a thin film of water, however, it can be created in any liquid, solid or gas) placed over the target tissue. (see, e.g., FIG. 46). The propagation of the wave towards the skin will increase the permeability of the stratum corneum. Subsequent to the formation of these pressure waves, the desired pharmaceutical can be applied.

Figure 41:
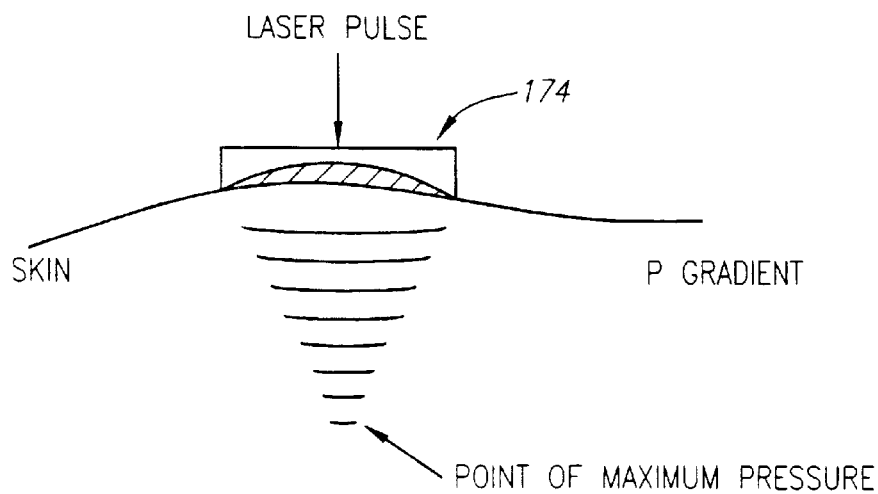
FIG. 41 shows the creation of pressure waves in tissue converging to a focal point.

In another embodiment, pressure gradients can be used to remove fluids, gases or other biomolecules from the body. This can be accomplished by focusing a beam of radiant energy down to a small volume at some point within the tissue. The resulting heating leads to pressure wave intensities (which are proportional to the degree of heating) that will be greater near the focal point of the radiant energy, and less near the surface. The consequence of this is a pressure gradient directed outwards thus enhancing the removal of fluids, gases or other biomolecules. Alternatively, propagating pressure waves created at the surface of the skin can be focused to a point within the tissue. This can be done, for example, by using a pulsed laser to irradiate a solid object 174 above the skin, which by virtue of its shape, induces pressure waves in the tissue which converges to the focal point (see, e.g., FIG. 41). Again, the consequence of this is a pressure gradient directed outwards thus enhancing the removal of fluids, gases or other biomolecules.

The pressure waves described can be created after perforation or alteration of the stratum corneum has taken place. Alternatively, pressure waves can be used as the sole means to increase the diffusive properties of compounds trough the skin or the removal of fluids, gases or other biomolecules.

Creation of Cavitation Bubbles to Increase Stratum Corneum Permeability

Cavitation bubbles, produced subsequent to the target tissues perforation or alteration, can be used to enhance the diffusive properties of a topically applied drug. While production of cavitation bubbles within the tissue is known (See, for example, R. Ensenaliev et al., "Effect of Tensile Amplitude and Temporal Characteristics on Threshold of Cavitation-Driven Ablation," Proc. SPIE vol. 2681, pp 326–333, (1996)), for the present invention, cavitation bubbles are produced in a material on or over the surface of the skin so that they propagate downwards (as they do because of conservation of momentum) and impact on the stratum corneum, thereby reducing the barrier function of the skin. The cavitation bubbles can be created in an absorbing material 170 located on or over the skin.

Cavitation has been seen to occur in water at −8 to −100 bars, (Jacques et al. Proc. SPIE vol. 1546, p. 284 (1992)). Thus, using a Q-switched Er:YAG laser (40 ns pulse) at 10 mJ and focussed to a spot size of 0.05 cm in a thin film of water on the skin, with a pulse repetition rate of 5–30 MHz, a stress of about 3750 bars, or 0.025 W/cm$^2$, is produced. This should generate the production of cavitation bubbles, which, when they contact the skin will cause mechanical and/or thermal damage thereby enhancing stratum corneum permeability.

In a preferred embodiment, the cavitation bubbles are produced in a thin film of water placed on or over the skin, however; any liquid or solid material can be used. Subsequent to production of the cavitation bubbles a pharmaceutical is applied to the affected tissue.

In an additional embodiment, cavitation bubbles are produced in the administered pharmaceutical subsequent to its application on the skin. Cavitation bubbles can also be produced in the stratum corneum itself before pharmaceutical application.

In a further embodiment, the target tissue is not perforated or altered before the production of cavitation bubbles, the cavitation bubbles' impact on the stratum corneum being the only method used to increase stratum corneum permeability.

Plasma Ablation to Increase Stratum Corneum Permeability

Plasma is a collection of ionized atoms and free electrons. It takes an extremely strong electric field or extremely high temperature to ionize atoms, but at the focus of an intense pulsed laser beam (>approx. $10^8$–$10^{10}$ $W/cm^2$), such electric fields can result. Above this energy fluence rate, high enough temperatures can result. What one sees when plasma is formed is a transient bright white cloud (which results from electrons recombining with atoms resulting in light emission at many different wavelengths which combine to appear to the eye as white). A loud cracking is usually heard when plasma is formed as a result of supersonic shock waves propagating out of the heated (>1000K) volume that has high pressures (perhaps >1000 atmospheres). Since plasma is a collection of hot energetic atoms and electrons, it can be used to transfer energy to other matter, such as skin. See Walsh J T, "Optical-Thermal Response of Laser-Irradiated Tissue," Chapter 25, pp. 865–902 (Plenum Press, NY 1995), incorporated by reference herein as if fully set forth in its entirety. For example, U.S. Pat. No. 5,586,981, issued to Hu, discloses the use of plasma to treat cutaneous vascular or pigmented lesions. The wavelength of the laser in Hu '981 is chosen such that the laser beam passes through the epidermal and dermal layers of skin and the plasma is created within the lesion, localizing the disruption to the targeted lesion.

A plasma can also be used to facilitate diffusion through the stratum corneum. In one embodiment of the present invention, plasma is produced above the surface of the skin whereupon a portion of the plasma cloud will propagate outwards (and downwards) to the skin whereupon, ablation or tissue alteration will occur. Plasma can be created in a liquid, solid or gas that is placed on or over the skin, into which the laser beam is focussed. If the plasma is created in a material with an acoustic impedance similar to tissue (say, a fluid), then the resulting pressure waves would tend to transfer most of their energy to the skin. The plasma "pressure wave" behaves similarly to propagating pressure waves. This is due to the fact that the acoustic impedance mismatch at the upper surface between air and solid/liquid material is high, and, furthermore, plasma, like ultrasonic energy propagates poorly in low-density (i.e. air) media.

In another embodiment, plasma is produced within the stratum corneum layer. Because the energy fluence rate needed to produce the plasma is as high as approximately $10^8$ $W/cm^2$, selection of a wavelength with radiant energy that is strongly absorbed in tissue is not an important concern.

Important benefits in these embodiments are that (1) the optical absorption of material to produce plasma is not an important consideration, although the energy fluence rate required to produce the plasma is less when the irradiated material strongly absorbs the incident radiant energy, and (2) there are relatively inexpensive diode-pumped Q-switched solid state lasers that can produce the requisite radiant energy (such as are available from Cutting Edge Optronics, Inc., St, Louis, Mo.).

To obtain a peak energy fluence rate greater than or approximately equal to the plasma creation threshold of $10^8$ $W/cm^2$, using a pulse length of 300 $\mu s$ (e.g. for the TRANSMEDICA™ Er:YAG laser, 1 J for 300 $\mu s$), the pulse power is 3333 W, and the spot size needs to be 0.0065 mm. Alternatively, a small diode-pumped Q-switched laser can be used. Such lasers have pulse widths on the order of 10 ns, and, as such, the requisite spot size for producing plasma could be much larger.

Continuous-Wave (CW) Laser Scanning

It is possible, under machine and microprocessor control, to scan a laser beam (either continuous-wave or pulsed) over the target tissue, and to minimize or eliminate thermal damage to the epidermis or adjacent anatomical structures.

For example, a scanner (made up of electro-optical or mechanical components) can be fashioned to continually move the laser beam over a user-defined area. This area can be of arbitrary size and shape. The path for the scan could be spiral or raster. If the laser is pulsed, or modulated, then it would be possible to do a discrete random pattern where the scanning optics/mechanics directs the beam to a site on the skin, the laser lases, and then the scanning optics/mechanics directs the beam to a different site (preferable not adjacent to the first spot so that the skin has time to cool before an adjacent spot is heated up).

This scanning technique has been used before with copper-vapor lasers (in treating port-wine stains) and is in use with $CO_2$ lasers for the purpose of facial resurfacing. In the case of the former, the subepidermal blood vessels are targeted, while in the latter, about 100 microns of tissue is vaporized and melted with each laser pass.

Interstitial Fluid Testing

Interstitial fluid contains concentrations of analytes that correlate with the concentration of analytes in other bodily fluids, such as blood. As such, the interstitial fluid analyte concentration can be tested to give an accurate measurement of analytes present in other bodily fluids.

One embodiment of the present invention is to perform testing on a number of analytes in the collected interstitial fluid sample to accurately measure levels of the analytes in other bodily fluids. For example, $Na^+$, $K^+$, $Ca^{++}$, $Mg^{++}$, $Cl^-$, $HCO_3^-$, $HHCO_3$, phosphates, $S_4^-$, glucose, amino-acid, cholesterol, phospholipids, neutral fat, $PO_2^-$, pH, organic acids and/or proteins are components of interstitial fluid and can be monitored. See N. Tietz, Textbook of Clinical Chemistry, W.B. Saunders Co., Philadelphia (1986), incorporated herein by reference. Interstitial fluid is, in many ways, filtered plasma, and has a similar constitution as plasma, except that some of the large proteins are filtered out by walls of the blood vessel. As such, components that can be assayed in serum can be assayed in interstitial fluid and such interstitial fluid components may be directly correlated to serum components. In one embodiment of this invention glucose in interstitial fluid is tested to monitor and treat blood sugar levels in diabetics.

Following the collection of interstitial fluid, as detailed above, the sample is tested for the specific analyte of interest, such as glucose. For glucose, testing can be done by infrared measurements, enzymatic analysis, or other testing protocols. Sodium and potassium are usually detected with ion-specific electrodes which allow a particular ion to penetrate an electrode, whereupon a current proportional to the ion concentration is produced and detected (analogous to a pH meter). Proteins are detected in various ways, for example, enzyme linked inununoassay (ELISA), gel electrophoresis, ultracentrifugation, radioimmunoassays, and fluorescence. These methodologies are discussed in N. Tietz, Textbook of Clinical Chemistry, W.B. Saunders Co., Philadelphia (1986).

There are a variety of substances that can be detected in interstitial fluid that are not normally present in apparently healthy individuals. Many of these substances are detected by colorimetry (after reacting the analyte with a test chemical), flame photometry, atomic absorption spectrometry, gas or mass spectrometry, and high-pressure liquid chromatography. For example, ethanol is detectable by reaction of the analyte with alcohol dehydrogenase, followed by colorimetry. These testing examples are not meant to limit the scope of the invention, but are merely embodiments.

In one embodiment the testing is completed as part of the laser perforation or alteration process. Using infrared radiation, for example, testing can be conducted in the container unit attached to the laser device. A section of the container unit, or the entire unit, is optionally constructed of a material that passes a predetermined light wavelength (e.g., for glucose, nylon, polyethylene or polyamide, which are partially transparent to infrared energy at 1040 nm, a wavelength absorbed by glucose, can be used). By sending light of known intensity through the container unit, as well as a reference beam sent through a portion of the container with no interstitial fluid, the absorption of the sample can be determined. A photosensitive diode, or other light detector is placed on the opposite side of the container unit from the light source. Absorption is determined by signals sent by the light detector. Based on absorption, the concentration of the analyte can then be determined. Specific techniques for conducting this type of infrared, or other spectrum analysis, can be found in U.S. Pat. No. 5,582,184, issued to Erickson et al. and D. A. Christensen, in Vol. 1648 Proceedings of Fiber Optic, Medical and Fluorescent Sensors and Applications, pp. 223–26 (1992), both incorporated herein by reference.

In a further embodiment of the present invention, following the collection of the interstitial fluid, the desired analyte is subjected to enzymatic means. For example, to determine glucose concentration, glucose can be oxidized using glucose oxidase. This creates gluconolactone and hydrogen peroxide. In the presence of colorless chromogen, the hydrogen peroxide is converted to water and a colored product. Because the intensity of the colored product is proportional to the amount of glucose, conventional absorbance or reflectance methods can be used to determine concentration. By calibrating the color to glucose concentration, the concentration of glucose can thereafter be visually approximated. Specific techniques for conducting this type of analysis can found in U.S. Pat. No. 5,458,140, issued to Eppstein et al., incorporated herein by reference.

In an additional embodiment of the present invention, the testing analysis can be electronically processed and fed to a digital readout, or other suitable means, on the lasing device.

In another embodiment of the present invention, the interstitial fluid is removed from the container unit, or the fluid is collected in a separate device. After collection, the above described testing methods can be conducted using separate equipment or by sending the sample to a testing laboratory.

In a further embodiment, after perforation or alteration, testing is completed on the tissue using separate methods or devices. For example, the 1994 monitoring technique described by N. Ito et al. ("Development of a Transcutaneous Blood-Constituent Monitoring Method Using a Suction Effusion Fluid Collection Technique and an Ion-Sensitive Field-Effect Transistor Glucose Sensor", vol. 32, No. 2, pp. 242–246, Medical & Biological Engineering & Computing, 1994), incorporated herein by reference, can be conducted at the site of perforation or alteration.

Delivery of a Pharmaceutical

A laser can be used to perforate or alter the skin through the outer surface, such as the stratum corneum layer, but not as deep as the capillary layer, to allow pharmaceuticals to be topically administered. Pharmaceuticals must penetrate the stratum corneum layer in order to be effective. Presently, compounds acting as drug carriers are used to facilitate the transdermal diffusion of some drugs. These carriers sometimes change the behavior of the drug, or are themselves toxic.

With the other parameters set, the intensity of the laser pump source will determine the intensity of the laser pulse, which will in turn determine the depth of the resultant perforation or alteration. Therefore, various settings on the laser can be adjusted to allow perforation or alteration of different thickness' of stratum corneum.

Optionally, a beam-dump can be positioned in such a way as not to impede the use of the laser for perforation or alteration of extremities. The beam-dump will absorb any stray electromagnetic radiation from the beam that is not absorbed by the tissue, thus, preventing any scattered rays from causing damage. The beam-dump can be designed so as to be easily removed for situations when the presence of the beam-dump would impede the placement of a body part on the applicator.

This method of delivering a pharmaceutical creates a very small zone in which tissue is irradiated, and only an extremely small zone of thermal necrosis. A practical round irradiation site can range from 0.1–5.0 cm in diameter, while a slit shaped hole can range from approximately 0.05–0.5 mm in width and up to approximately 2.5 mm in length, although other slit sizes and lengths can be used. As a result, healing is quicker than or as quick as the healing after a skin puncture with a sharp implement. After irradiation, pharmaceuticals can then be applied directly to the skin or in a pharmaceutically acceptable formulation such as a cream, ointment, lotion or patch.

Alternatively, the delivery zone can be enlarged by strategic location of the irradiation sites and by the use of multiple sites. The present method can be used for transport of a variety of pharmaceuticals. For example, a region of skin may be anesthetized by first scanning the desired area with a pulsing laser such that each pulse is sufficient to cause perforation or alteration. This can be accomplished with modulated diode or related microchip lasers, which deliver single pulses with temporal widths in the 1 femtosecond to 1 ms range. Anesthetic (e.g., 10% lidocaine) would then be applied over the treated area to achieve a zone of anesthesia.

Figure 11:
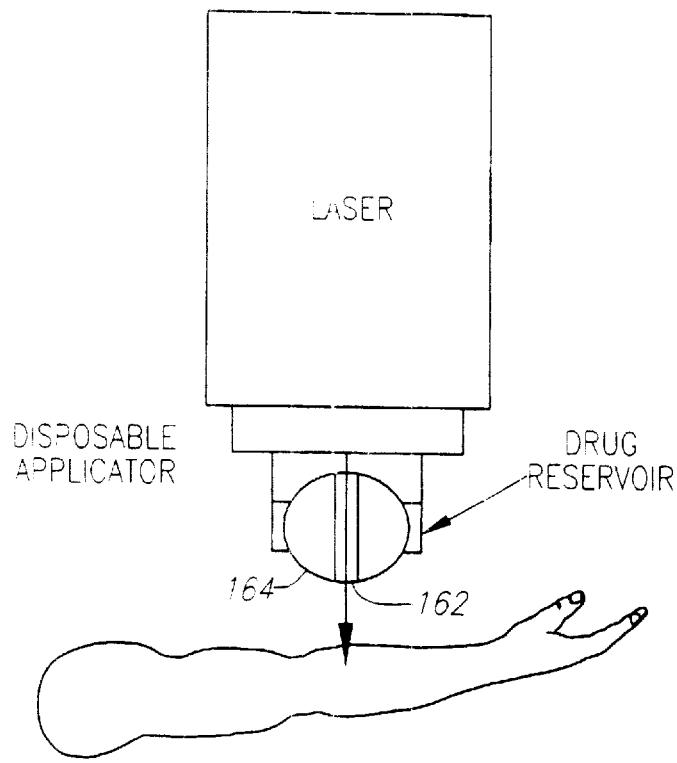
FIG. 11 shows a roll-on device for the delivery of pharmaceuticals.

According to one embodiment of the present invention, a pharmaceutical is administered immediately after the analyte of interest has been measured. For example, in the case of glucose, after measurement, a signal can be sent to a drug reservoir to deliver an appropriate amount of insulin. Two embodiments of this invention incorporate an atomizer (FIG. 18) or a roll-on device (FIG. 11). In the case of a roll-on device, the laser beam propagates through hole 162 incorporated in ball 164 of the roll-on device. In the alternative, the roll-on device can be positioned adjacent to the path of the laser beam through the disposable applicator. After measurement, if needed, the roll-on device is rolled over the irradiated site, thereby administering the desired pharmaceutical. In the case of an atomizer, the pharmaceutical is administered from a drug reservoir 166 through the use of compressed gas. After measurement of the desired analyte, a cylinder 168 containing compressed gas (such as, for example, carbon dioxide) can be triggered to spray a set amount of pharmaceutical, such as insulin, over the irradiated site.

In another embodiment of the present invention, an ink jet or mark is used for marking the site of irradiation. The irradiated sites are often not easily visible to the eye, consequently the health care provider may not know exactly where to collect the fluid sample or to apply the pharmaceutical. This invention further provides techniques to mark the skin so that the irradiation site is apparent. For example, an ink-jet (analogous to those used in ink-jet printers) can be engaged prior to, during or immediately after laser irradiation. Additionally, a circle can be marked around the irradiation site, or a series of lines all pointing inward to the irradiation site can be used. Alternatively, a disposable safety-tip/applicator can be marked on the end (the end that touches up against the skin of the patient) with a pigment. Engaging the skin against the applicator prior to, during, or immediately after lasing results in a mark on the skin at the site of irradiation.

Figure 42:
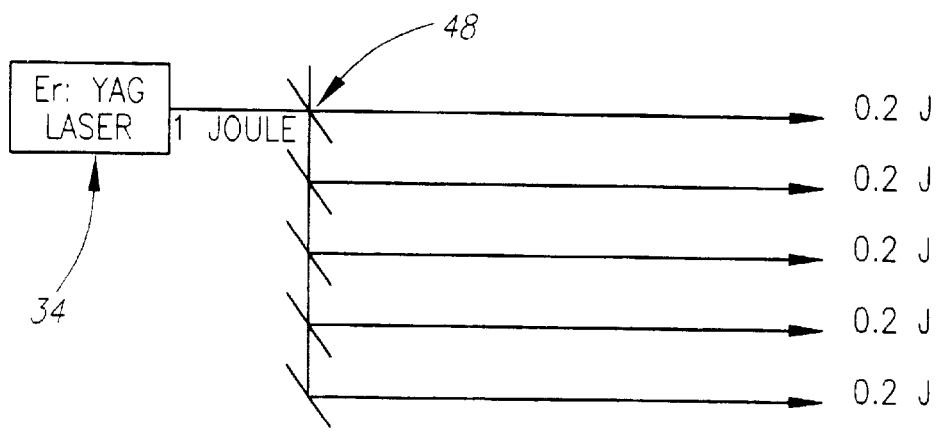
FIG. 42 shows an example of a beam splitter suitable for making simultaneous irradiation sites.
Figure 43:
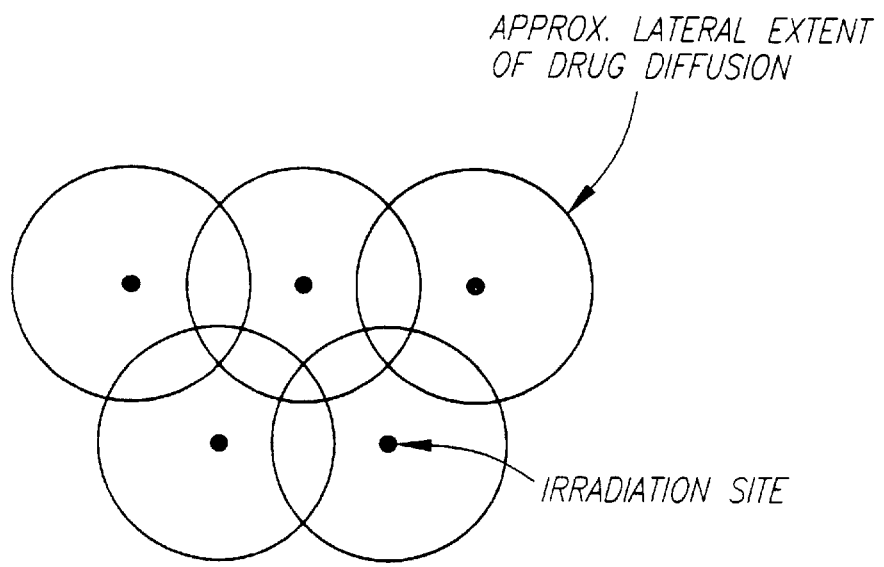
FIG. 43 shows one possible pattern of perforation or alteration sites using a beam splitter.

For certain purposes, it is useful to create multiple perforations or alterations of the skin simultaneously or in rapid sequence. To accomplish this, a beam-splitter or multiply pulsed laser can optionally be added to the laser or a rapidly pulsing laser, such as a diode or related microchip laser, may be used. Multiple irradiated sites, created simultaneously or sequentially, would result in an increased uptake of drugs as compared to a single irradiation site (i.e. an increase in uptake proportional to the total number of ablated sites). An example of a beam splitter 48 suitable for making simultaneous irradiation sites can be found in FIG. 42. Any geometric pattern of spots can be produced on the skin using this technique. Because the diffusion of fluid out of the skin or drugs into skin can be approximated as symmetric, a beneficial pattern of irradiation spots (such that a uniform local concentration would result over as wide an area as possible) would be to position each spot equidistant from each other in a staggered matrix pattern (FIG. 43).

Alternatively, multiple irradiation sites, or an irradiated area of arbitrary size and shape, could be produced with use of a scanner. For example, oscillating mirrors which reflect the beam of laser radiant energy can operate as a scanner.

For application of the laser device in fluid removal or pharmaceutical delivery, the laser is manipulated in such a way that a portion of the patient's skin is positioned at the site of the laser focus within the applicator. For perforations or alterations for fluid, gas or other biomolecule removal or pharmaceutical delivery, a region of the skin which has less contact with hard objects or with sources of contamination is preferred, but not required. Examples are skin on the arm, leg, abdomen or back. Optionally, the skin heating element is activated at this time in order to reduce the laser energy required for altering or ablating the stratum corneum.

Figure 2:
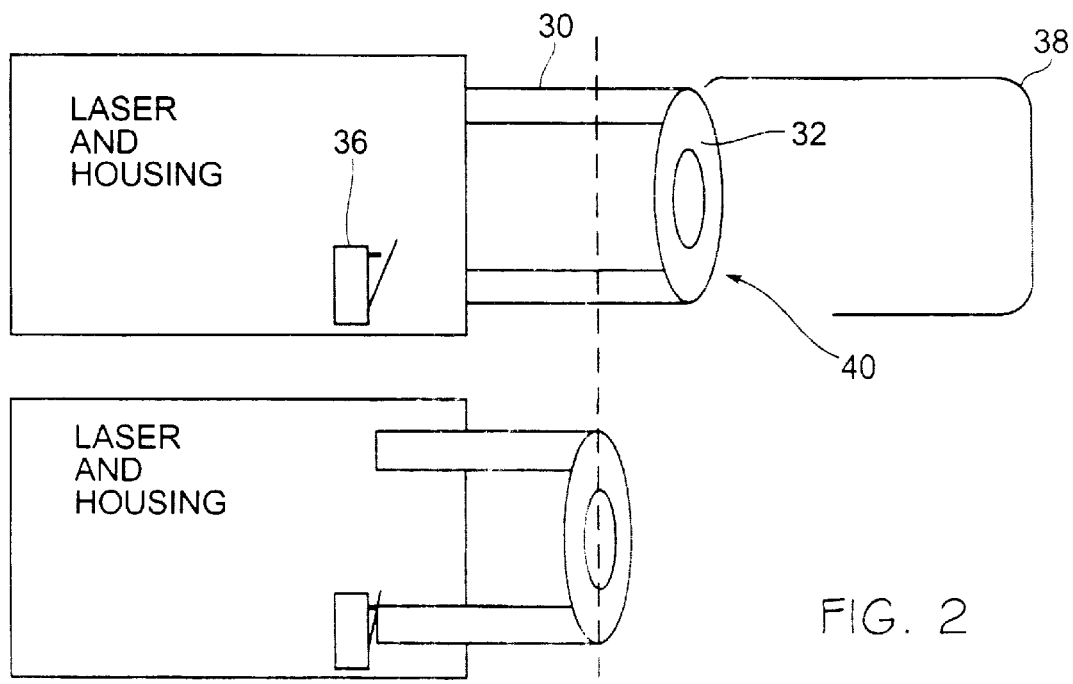
FIG. 2 shows an optional spring-loaded interlock and optionally heated applicator.

Preferably a holder is provided with a hole coincident with the focal plane of the optical system. Optionally, as shown in FIG. 2, a spring-loaded interlock 36 can be attached to the holder, so that when the patient applies a small amount of pressure to the interlock, to recess it to the focal point, a switch is closed and the laser will initiate a pulse of radiation. In this setup, the focal point of the beam is not in line with the end of the holder until that end is depressed. In the extremely unlikely event of an accidental discharge of the laser before proper positioning of the tissue at the end of the laser applicator, the optical arrangement will result in an energy fluence rate that is significantly low, thus causing a negligible effect on unintentional targets.

The method of this invention may be enhanced by using a laser of a wavelength that is specifically absorbed by the skin components of interest (e.g., water, lipids or protein) which strongly affect the permeation of the skin tissues. Altering the lipids in stratum corneum may allow enhanced permeation while avoiding the higher energies that are necessary to affect the proteins and water.

It would be beneficial to be able to use particular lasers other than the Er:YAG for perforation or alteration of tissue. For example, diode lasers emitting radiant energy with a wavelength of 910 nm (0.8 microns) are inexpensive, but such wavelength radiation is only poorly absorbed by tissue. In a further embodiment of this invention, a dye is administered to the skin surface, either by application over intact stratum corneum, or by application over an Er:YAG laser treated site (so the that deep dye penetration can occur), that absorbs such a wavelength of radiation. For example, indocyanine green (ICG), which is a harmless dye used in retina angiography and liver clearance studies, absorbs maximally at 810 nm when in plasma (Stephen Flock and Steven Jacques, "Thermal Damage of Blood Vessels in a Rat Skin-Flap Window Chamber Using Indocyanine Green and a Pulsed Alexandrite Laser: A Feasibility Study", Laser Med. Sci. 8, 185–196, (1993)). This dye, when in stratum corneum, is expected to absorb the 810 nm radiant energy from a diode laser (e.g. a GaAlAs laser) thereby raising the temperature of the tissue, and subsequently leading to ablation or molecular changes resulting in reduced barrier function.

Alternatively, it is possible to chemically alter the optical properties of the skin to enhance subsequent laser radiant energy absorption without chemicals actually being present at the time of laser irradiation. For example, 5-aminolevulinic acid (5-ALA) is a precursor to porphyrins, which are molecules involved in hemoglobin production and behavior. Porphyrins are strong absorbers of light. Administration of 5-ALA stimulates production of porphyrins in cells, but is itself consumed in the process. Subsequently, there will be enhanced absorption of radiant energy in this tissue at wavelengths where porphyrins absorb (e.g., 400 mm or 630 mm).

Another way to enhance the absorption of radiant energy in stratum corneum without the addition of an exogenous absorbing compound is to hydrate the stratum corneum by, for example, applying an occlusive barrier to the skin prior to laser irradiation. In this situation, the water produced within the body itself continues to diffuse through the stratum corneum and propagate out through pores in the skin, but is prevented from evaporating by the occlusive barrier. Thus, the moisture is available to further saturate the stratum corneum. As the radiant energy emitted by the Er:YAG laser is strongly absorbed by water, this process would increase the absorption coefficient of the stratum corneum, and so less energy would be required to induce the alterations or ablations in the stratum corneum necessary for enhanced topical drug deliver.

Additionally, the laser irradiated site eventually heals as a result of infiltration of keratinocytes and keratin (which takes perhaps two weeks to complete), or by the diffusion of serum up through the ablated sites which form a clot (or eschar) which effectively seals the ablated site. For long term fluid collection and measurement, topical delivery of drugs, or for multiple sequential administrations of topical drugs, it would be beneficial to keep the ablated site open for an extended length of time.

Thus, in an additional embodiment of this invention, the ablated or non-ablated site is kept open by keeping the area of irradiation moist and/or biochemically similar to stratum corneum. This is accomplished by minimizing contact of air with the ablated site and/or providing fluid to keep the ablated site moist. The application of a patch (containing, for example, an ointment such as petroleum jelly or an ointment containing hydrocortisone) over the site would help to keep it open. A hydrogel patch would also serve to provide the necessary moisture. Additionally, cytotoxic drugs such as cisplatin, bleomycin, doxorubicin, and methotrexate, for example, topically applied in low concentrations would locally prevent cellular infiltration and wound repair. Furthermore, application of a vitamin C (ascorbic acid) or other known inhibitors of melanin production, following irradiation, would help to prevent additional skin coloration in the area, following treatment.

Alteration Without Ablation

There are advantages to the technique of altering and not ablating the stratum corneum. In a preferred embodiment, the skin is altered, not ablated, so that its structural and biochemical makeup allows fluid to diffuse to the skin surface and allows drugs to permeate. The consequence of this embodiment is: (1) the skin after irradiation still presents a barrier, albeit reduced, to external factors such as viruses and chemical toxins; (2) less energy is required than is required to ablate the stratum corneum, thus smaller and cheaper lasers can be used; and (3) less tissue damage occurs, thus resulting in more rapid and efficient healing.

Radiant Energy vs Laser Radiant Energy

The radiant energy emitted by lasers has the properties of being coherent, monochromatic, collimated and (typically) intense. Nevertheless, to enhance transdermal drug delivery or fluid, gas or biomolecule collection, the radiant energy-used need not have these properties, or alternatively, can have one of all of these properties, but can be produced by a non-laser source.

For example, the pulsed light output of a pulsed xenon flashlamp can be filtered with an optical filter or other wavelength selection device, and a particular range of wavelengths can be selected out of the radiant energy output. While the incoherent and quasimonochromatic output of such a configuration cannot be focussed down to a small spot as can coherent radiant energy, for the aforementioned purpose that may not be important as it could be focused down to a spot with a diameter on the order of millimeters. Such light sources can be used in a continuous wave mode if desirable.

The infrared output of incandescent lights is significantly more than their output in the visible, and so such light sources, if suitably filtered to eliminate undesirable energy that does not reduce barrier function, could be used for this purpose. In another embodiment of the invention, it would be possible to use an intense incandescent light (such as a halogen lamp), filter it with an optical filter or similar device, and used the continuous-wave radiant energy output to decrease the barrier function of stratum corneum without causing ablation. All of these sources of radiant energy can be used to produce pulses, or continuos-wave radiant energy.

Laser Device

The practice of the present invention has been found to be effectively performed by various types of lasers; for example, the TRANSMEDICA™ Er:YAG laser skin perforator, or the Schwartz Electro-Optical Er:YAG laser. Any pulsed laser producing energy that is strongly absorbed in tissue may be used in the practice of the present invention to produce the same result at a nonablative wavelength, pulse length, pulse energy, pulse number, and pulse rate. However, lasers which produce energy that is not strongly absorbed by tissue may also be used, albeit less effectively, in the practice of this invention. Additionally, as described herein, continuous-wave lasers may also be used in the practice of this invention.

FIGS. 1 and 2 are diagrammatic representations a typical laser that can be used for this invention. As shown in FIGS. 1 and 2, a typical laser comprises a power connection which can be either a standard electrical supply 10, or optionally a rechargeable battery pack 12, optionally with a power interlock switch 14 for safety purposes; a high voltage pulse-forming network 16; a laser pump-cavity 18 containing a laser rod 20, preferably Er:YAG; a means for exciting the laser rod, preferably a flashlamp 22 supported within the laser pump-cavity; an optical resonator comprised of a high reflectance mirror 24 positioned posterior to the laser rod and an output coupling mirror 26 positioned anterior to the laser rod; a transmitting focusing lens 28 positioned beyond the output coupling mirror; optionally a second focusing cylindrical lens 27 positioned between the output coupling mirror and the transmitting focusing lens; an applicator 30 for positioning the subject skin at the focal point of the laser beam, which is optionally heated for example with a thermoelectric heater 32, attached to the laser housing 34; an interlock 36 positioned between the applicator and the power supply; and optionally a beam dump 38 attached to the applicator with a fingertip access port 40.

The laser typically draws power from a standard 110 V or 220 V AC power supply 10 (single phase, 50 or 60 Hz) which is rectified and used to charge up a bank of capacitors included in the high voltage pulse-forming network 16. Optionally, a rechargeable battery pack 12 can be used instead. The bank of capacitors establishes a high DC voltage across a high output flashlamp 22. Optionally a power interlock 14, such as a key switch, can be provided which will prevent accidental charging of the capacitors and thus accidental laser excitation. A further interlock can be added to the laser at the applicator, such as a spring-loaded interlock 36, so that discharge of the capacitors requires both interlocks to be enabled.

With the depression of a switch, a voltage pulse can be superimposed on the already existing voltage across the flashlamp in order to cause the flashlamp to conduct, and, as a consequence, initiate the flash. The light energy from the flashlamp is located in the laser cavity 18 that has a shape such that most of the light energy is efficiently directed to the laser rod 20, which absorbs the light energy, and, upon de-excitation, subsequently lases. The laser cavity mirrors of low 26 and high 24 reflectivity, positioned collinearly with the long-axis of the laser rod, serve to amplify and align the laser beam.

Figure 12:
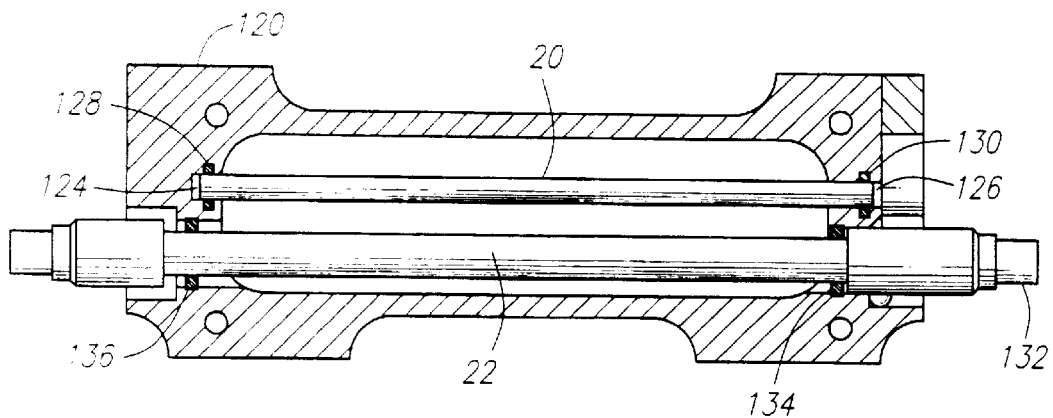
FIG. 12 shows an elastomeric mount for a solid state laser crystal element with optional mirrored surfaces applied to each end of the element.

Optionally, as shown in FIG. 12 the laser cavity mirrors comprise coatings 124, 126, applied to ends of the crystal element and which have the desired reflectivity characteristics. In a preferred embodiment an Er:YAG crystal is grown in a boule two inches in diameter and five inches long. The boule is core drilled to produce a rod 5–6 millimeters in diameter and five inches long. The ends of the crystal are ground and polished. The output end, that is the end of the element from which the laser beam exits, is perpendicular to the center axis of the rod within 5 arc minutes. The flatness of the output end is 1/10 a wavelength (2.9 microns) over 90% of the aperture. The high reflectance end, that is the end opposite the output end, comprises a two meter convex spherical radius. The polished ends are polished so that there are an average of ten scratches and five digs per Military Specification Mil-0-13830A. Scratch and dig are subjective measurements that measure the visibility of large surface defects such as defined by U.S. military standards. Ratings consist of two numbers, the first being the visibility of scratches and the latter being the count of digs (small pits). A #10 scratch appears identical to a 10 micron wide standard scratch while a #1 dig appears identical to a 0.01 mm diameter standard pit. For collimated laser beams, one normally would use optics with better than a 40–20 scratch-dig rating.

Many coatings are available from Rocky Mountain Instruments, Colorado Springs, Colo. The coating is then vacuum deposited on the ends. For a 2.9 micron wavelength the coatings for the rear mirrored surface 124 should have a reflectivity of greater than 99%. The coating for the output end surface, by contrast, should have a reflectance of between 93% and 95%, but other mirrored surfaces with reflectivity as low as 80% are useful. Other vacuum deposited metallic coatings with known reflectance characteristics are widely available for use with other laser wavelengths.

The general equation which defines the reflectivity of the mirrors in a laser cavity necessary for the threshold for population inversion is:

$$R_1 R_2 (1-a_L)^2 \exp[(g_{21}-\alpha)2L]=1$$

where the $R_1$ and $R_2$ are the mirrors' reflectivities, $a_L$ is the total scattering losses per pass through the cavity, $g_{21}$ is the gain coefficient which is the ratio of the stimulated emission cross section and population inversion density, a is the absorption of the radiation over one length of the laser cavity, and L is the length of the laser cavity. Using the above equation, one can select a coating with the appropriate spectral reflectivity from the following references. W. Driscoll and W. Vaughan, "Handbook of Optics," ch. 8, eds., McGraw-Hill: NY (1978); M. Bass, et al., "Handbook of Optics," ch. 35, eds., McGraw Hill: NY (1995).

Optionally, as also shown in FIG. 12, the crystal element may be non-rigidly mounted. In FIG. 12 an elastomeric material O-ring 128 is in a slot in the laser head assembly housing 120 located at the high reflectance end of the crystal element. A second elastomeric material O-ring 130 is in a second slot in the laser head assembly at the output end of the crystal element. The O-rings contact the crystal element by concentrically receiving the element as shown. However, elastomeric material of any shape may be used so long as it provides elastomeric support for the element (directly or indirectly) and thereby permits thermal expansion of the element. Optionally, the flash lamp 22 may also be non-rigidly mounted. FIG. 12 shows elastomeric O-rings 134, 136, each in its own slot within the laser head assembly housing. In FIG. 12 the O-rings 134 and 136 concentrically receive the flash lamp. However, the flash lamp may be supported by elastomeric material of other shapes, including shapes without openings.

Figure 3:
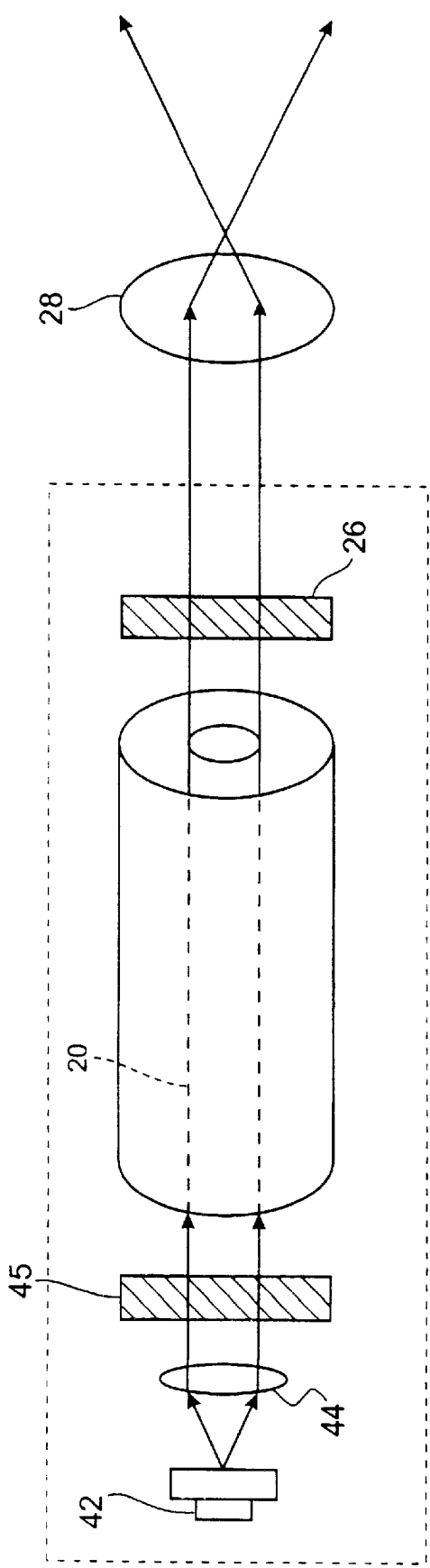
FIG. 3 shows an alternative means of exciting a laser rod using a diode laser.
Figure 6:
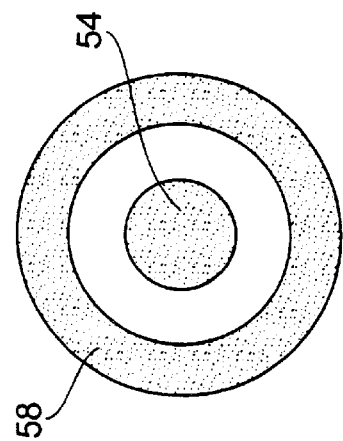
FIG. 6 shows a patch which can be used to sterilize the perforation site.

Optionally, as shown in FIG. 3, a diode laser 42 that produces a pump-beam collinear with the long-axis of the laser crystal can be used instead of the flashlamp to excite the crystal. The pump-beam of this laser is collimated with a collimating lens 44, and transmitted to the primary laser rod through the high reflectance infrared mirror 45. This high reflectance mirror allows the diode pump laser beam to be transmitted, while reflecting infrared light from the primary laser.

The Er:YAG lasing material is the preferred material for the laser rod because the wavelength of the electromagnetic energy emitted by this laser, 2.94 microns, is very near one of the peak absorption wavelengths (approximately 3 microns) of water. Thus, this wavelength is strongly absorbed by water and tissue. The rapid heating of water and tissue causes perforation or alteration of the skin.

Other useful lasing material is any material which, when induced to lase, emits a wavelength that is strongly absorbed by tissue, such as through absorption by water, nucleic acids, proteins or lipids and consequently causes the required perforation or alteration of the skin (although strong absorption is not required). A laser can effectively cut or alter tissue to create the desired perforations or alterations where tissue exhibits an absorption coefficient of 10–10,000 $cm^{-1}$. Examples of useful lasing elements are pulsed $CO_2$ lasers, Ho:YAG (holmium:YAG), Er:YAP, Er/Cr:YSGG (erbium/chromium: yttrium, scandium, gallium, garnet; 2.796 microns), Ho:YSGG (holmium: YSGG; 2.088 microns), Er:GGSG (erbium: gadolinium, gallium, scandium, garnet), Er:YLF (erbium: yttrium, lithium, fluoride; 2.8 microns), Trn:YAG (thulium: YAG; 2.01 microns), Ho:YAG (holmium: YAG; 2.127 microns); Ho/Nd:YA103 (holmiumlneodymium: yttrium, aluminate; 2.85–2.92 microns), cobalt:$MgF_2$ (cobalt: magnesium fluoride; 1.75–2.5 microns), HF chemical (hydrogen fluoride; 2.6–3 microns), DF chemical (deuterium fluoride; 3.6–4 microns), carbon monoxide (5–6 microns), deep UV lasers, and frequency tripled Nd:YAG (neodymium:YAG, where the laser beam is passed through crystals which cause the frequency to be tripled).

Utilizing current technology, some of these laser materials provide the added benefit of small size, allowing the laser to be small and portable. For example, in addition to Er:YAG, Ho:YAG lasers also provide this advantage.

Figure 13:
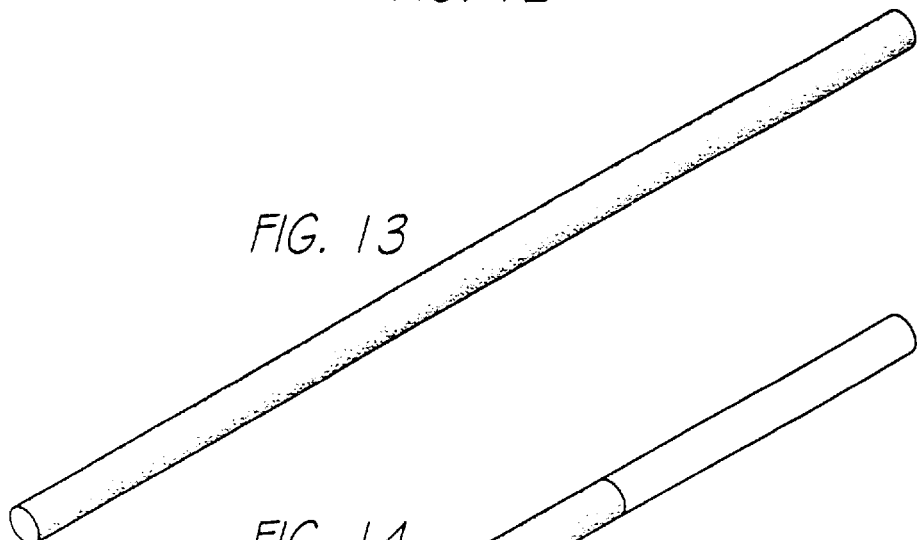
FIG. 13 shows an example of a crystal rod with matte finish around the full circumference of the entire rod.
Figure 14:
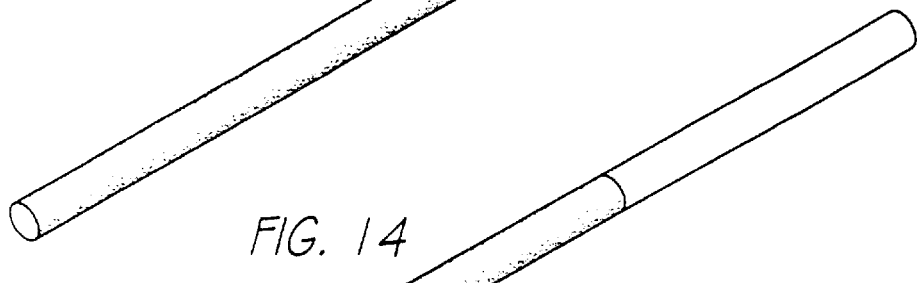
FIG. 14 shows an example of a crystal rod with matte finish around the full circumference of two-thirds of the rod.
Figure 15:
FIG. 15 shows an example of a crystal rod with matte stripes along its longitudinal axis.

Solid state lasers, including but not limited to those listed above, may employ a polished barrel crystal rod. The rod surface may also contain a matte finish as shown in FIG. 13. However, both of these configurations can result in halo rays which surround the central output beam. Furthermore, an all-matte finish, although capable of diminishing halo rays relative to a polished rod, will cause a relatively large decrease in the overall laser energy output. In order to reduce halo rays and otherwise affect beam mode, the matte finish can be present on bands of various lengths along the rod, each band extending around the entire circumference of the rod. Alternatively, the matte finish may be present in bands along only part of the rod's circumference. FIG. 14 shows a laser crystal element in which the matte finish is present upon the full circumference of the element along two-thirds of its length. Alternatively, as shown in FIG. 15, matte stripes may be present longitudinally along the full length of the rod. The longitudinal stripes may alternatively exist along only part of the length of the rod, such as in stripes of various lengths. A combination of the foregoing techniques may be used to affect beam shape. Other variations of patterns may also be employed in light of the beam shape desired. The specific pattern may be determined based on the starting configuration of the beam from a 100% polished element in light of the desired final beam shape and energy level. A complete matte finish element may also be used as the starting reference point.

For purposes of beam shape control, any surface finish of greater than 30 microinches is considered matte. A microinch equals one millionth (0.000001) inch, which is a common unit of measurement employed in establishing standard roughness unit values. The degree of roughness is calculated using the root-mean-square average of the distances in nicroinches above or below the mean reference line, by taking the square root of the mean of the sum of the squares of these distances. Although matte surfaces of greater than 500 microinches may be used to affect beam shape, such a finish will seriously reduce the amount of light energy that enters the crystal rod, thereby reducing the laser's energy.

To remove the beam halo, a matte area of approximately 50 microinches is present around the full circumference of an Er:YAG laser rod for two-thirds the length of the rod. The non-matte areas of the rod are less than 10 microinches. A baseline test of the non-matte rod can be first conducted to determine the baseline beam shape and energy of the rod. The matte areas are then obtained by roughing the polished crystal laser rod, such as with a diamond hone or grit blaster. The specific pattern of matte can be determined with respect to the desired beam shape and required beam energy level. This results in a greatly reduced beam halo. The rod may also be developed by core drilling a boule of crystal so that it leaves an overall matte finish and then polishing the desired areas, or by refining a partially-matte, partially polished boule to achieve the desired pattern.

Figure 16:
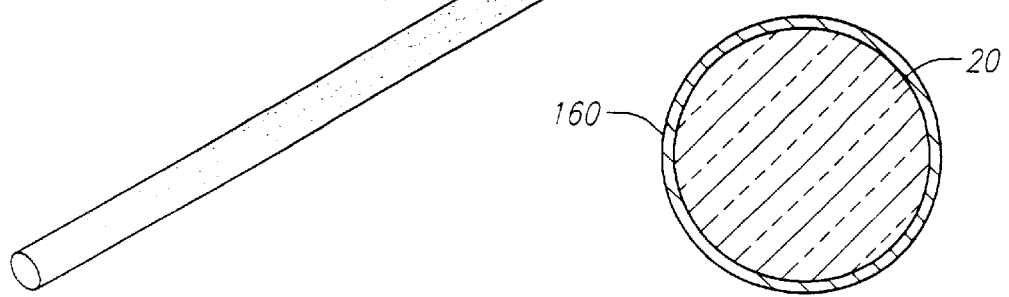
FIG. 16 shows a cross-section of a crystal laser rod element surrounded by a material having an index of refraction greater than the index of refraction of the rod.

The beam shape of a crystal laser rod element may alternatively be modified as in FIG. 16 by surrounding the rod 20 in a material 160 which is transparent to the exciting light but has an index of refraction greater than the rod. Such a modification can reduce the halo of the beam by increasing the escape probability of off-axis photons within the crystal. This procedure may be used in place of or in addition to the foregoing matte procedure.

The emitted laser beam is focused down to a millimeter or submillimeter sized spot with the use of the focusing lens 28. Consideration of laser safety issues suggests that a short focal length focusing lens be used to ensure that the energy fluence rate (W/cm$^2$) is low except at the focus of the lens where the tissue sample to be perforated or altered is positioned. Consequently, the hazard of the laser beam is minimized.

The beam can be focused so that it is narrower along one axis than the other in order to produce a slit-shaped perforation or alteration through the use of a cylindrical focusing lens 27. This lens, which focuses the beam along one axis, is placed in series with the transmitting focusing lens 28. When perforations or alterations are slit-shaped, the patient discomfort or pain associated with the perforation or alteration is considerably reduced.

Figure 4:
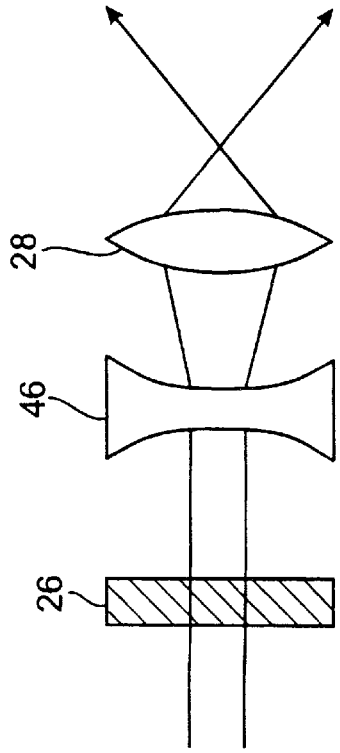
FIG. 4 shows an alternative focusing mechanism.

Optionally, the beam can be broadened, for instance through the use of a concave diverging lens 46 (FIG. 4) prior to focusing through the focusing lens 28. This broadening of the beam results in a laser beam with an even lower energy fluence rate a short distance beyond the focal point, consequently reducing the hazard level. Furthermore, this optical arrangement reduces the optical aberrations in the laser spot at the treatment position, consequently resulting in a more precise perforation or alteration.

Figure 5A:
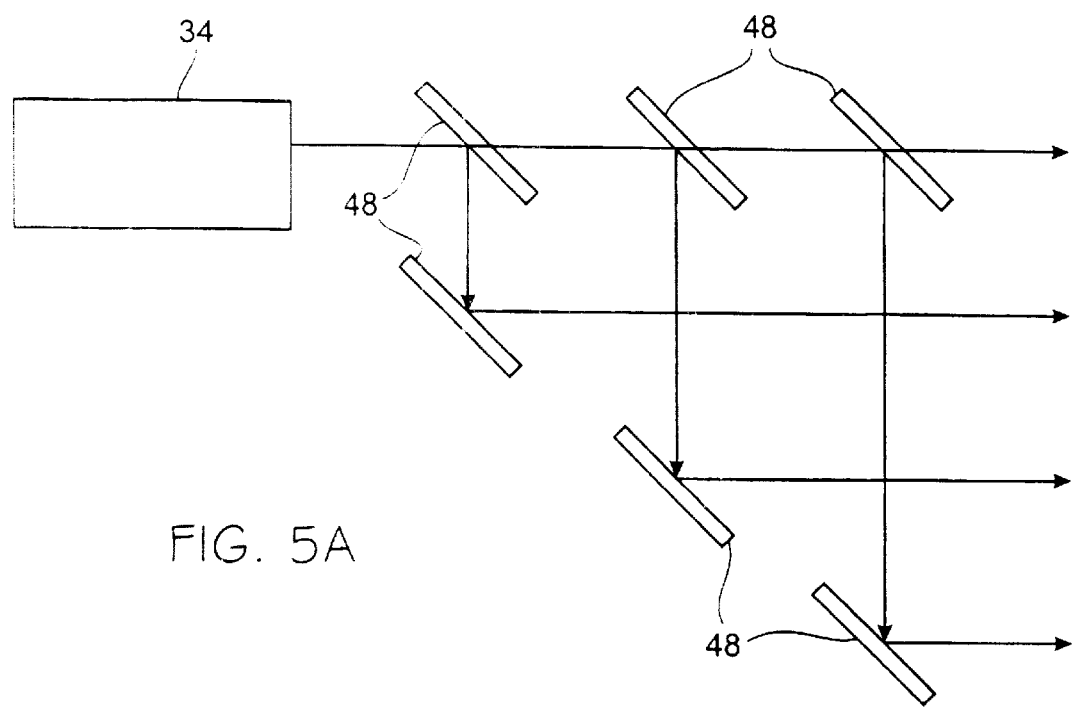
FIGS. 5A & 5B show optional beam splatters for creating multiple simultaneous irradiation.
Figure 5B:
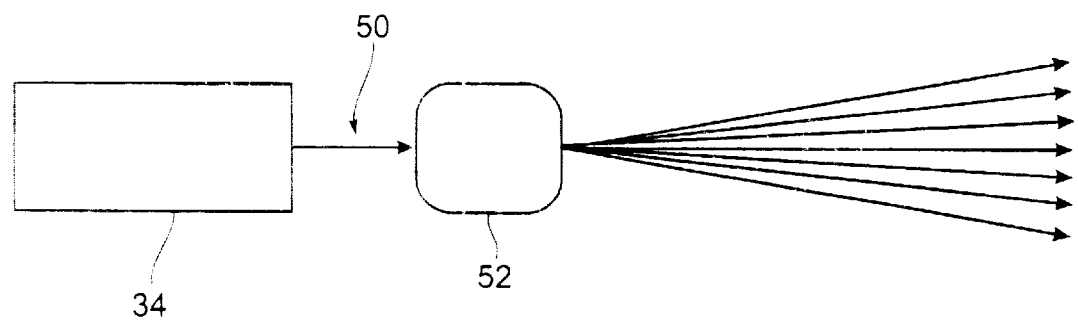
Figure 7A:

Also optionally, the beam can be split by means of a beam-splitter to create multiple beams capable of perforating or altering several sites simultaneously or near simultaneously. FIG. 5 provides two variations of useful beam splitters. In one version, multiple beam splitters 48 such as partially silvered mirrors, dichroic mirrors, or beam-splitting prisms can be provided after the beam is focused. Alternatively, an acousto-optic modulator 52 can be supplied with modulated high voltage to drive the modulator 52 and bend the beam. This modulator is outside the laser cavity. It functions by deflecting the laser beam sequentially and rapidly at a variety of angles to simulate the production of multiple beams.

Portability

Currently, using a portable TRANSMEDICAT™ Er:YAG laser, the unit discharges once per 20–30 seconds. This can be increased by adding a battery and capacitor and cooling system to obtain a quicker cycle. Multiple capacitors can be strung together to get the discharge rate down to once every 5 or 10 seconds (sequentially charging the capacitor banks). Thus, getting a higher repetition rate than with a single capacitor.

The TRANSMEDICA™ Er:YAG laser incorporates a flashlamp, the output of which is initiated by a high-voltage pulse of electricity produced by a charged capacitor bank. Due to the high voltages required to excite the flashlamp, and because the referred to version of the laser incorporates dry cells to run (thus the charging current is much less than a wall-plug could provide), then the capacitors take about 20 seconds to sufficiently charge Thus, if a pulse repetition rate of 1 pulse/20 seconds is desirable, it would be suitable to have multiple capacitor banks that charge sequentially (i.e. as one bank fires the flashlamp, another bank, which has been recharging, fires, and so on). Thus, the pulse repetition rate is limited only be the number of capacitor banks incorporated into the device (and is also limited by the efficiency of waste-heat removal from the laser cavity).

A small heater, such as a thermoelectric heater 32, is optionally positioned at the end of the laser applicator proximal to the site of perforation. The heater raises the temperature of the tissue to be perforated or altered prior to laser irradiation. This increases the volume of fluid collected when the device is used for that purpose. A suggested range for skin temperature is between 36° C. and 45° C., although any temperature which causes vasodilation and the resulting increase in blood flow without altering the blood chemistry is appropriate.

Container Unit

Figure 8:
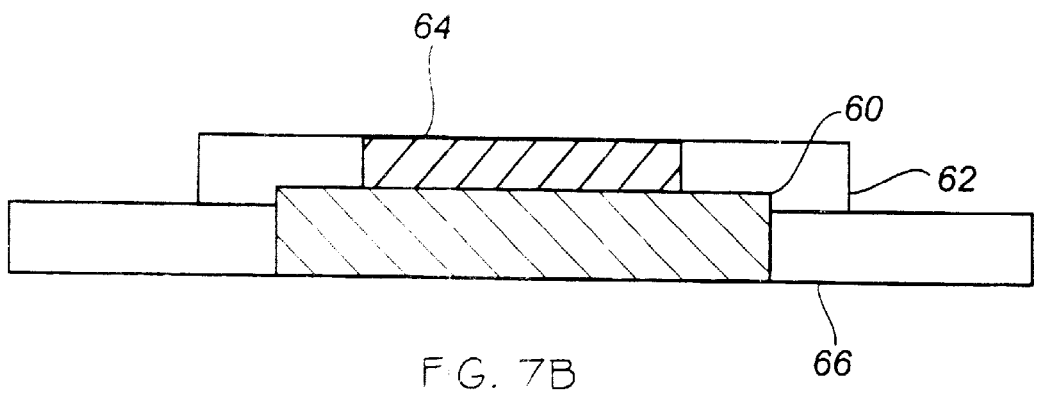
FIG. 8 shows an optional container unit for collecting fluids, ablated tissue, and/or other matter released from the site of irradiation, and for reducing noise resulting from the interaction between the laser and the patient's tissue.
Figure 8:
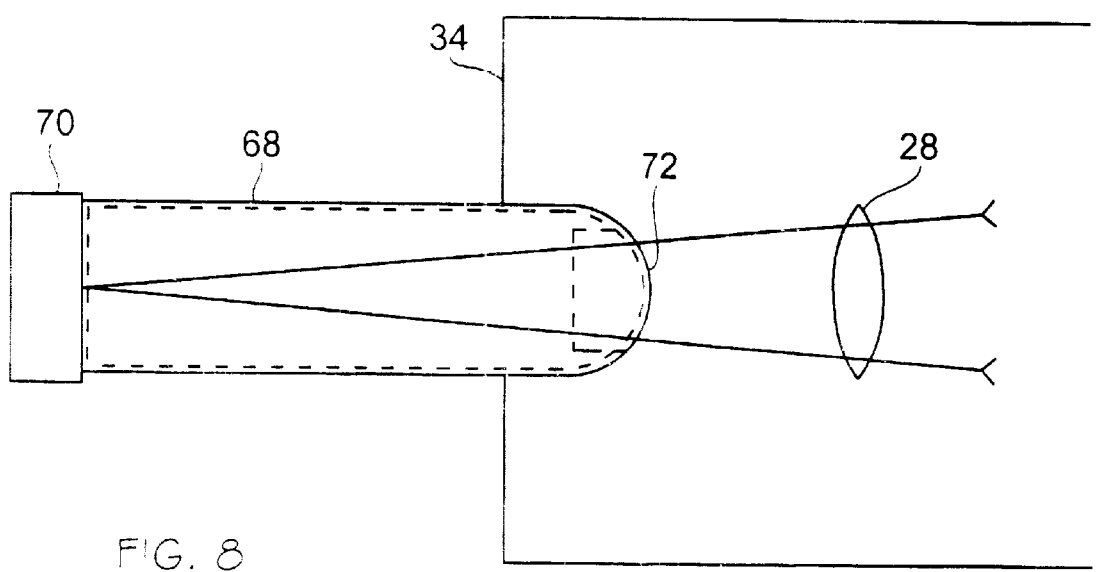

A container unit 68 is optionally fitted into the laser housing and is positioned proximal to the site of irradiation. The container unit reduces the intensity of the sound produced when the laser beam perforates the patient's tissue, increases the efficiency of interstitial fluid collection, and collects the ablated tissue and other matter released by irradiation. The container unit is shaped so as to allow easy insertion into the laser housing and to provide a friction fit within the laser housing. FIG. 8 shows the container unit inserted into the laser housing and placed over the site of irradiation.

The container unit 68 comprises a main receptacle 82, including a lens 84. The main receptacle collects the interstitial fluid sample, the ablated tissue, and/or other matter released by irradiation. The lens is placed such that the laser beam may pass through the lens to the site of irradiation but so that the matter released by irradiation does not splatter back onto the applicator. The container unit also optionally includes a base 86, attached to the receptacle. The base can optionally be formed so at to be capable of being inserted into the applicator to disengage a safety mechanism of the device, thereby allowing the laser beam to be emitted.

As shown in FIG. 17, the shape and size of the container unit 68 are such as to allow placement next to or insertion into the applicator, and to allow collection of the interstitial fluid sample, ablated tissue, and/or other matter released by irradiation. Examples of shapes that the main receptacle may take include cylinders, bullet shapes, cones, polygons and free form. shapes. Preferably, the container unit has a main receptacle, with a volume of around 1–2 milliliters. However, larger and smaller receptacles will also work.

Figure 20:
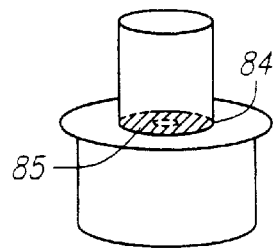
FIG. 20 shows an example of a lens with a mask.

The lens 84, which allows the laser beam to pass through while preventing biological and other matter from splattering back onto the applicator, is at least partially transparent. The lens is constructed of a laser light-transmitting material and is positioned in the pathway of the laser beam, at the end of the container unit proximal to the beam. In one embodiment, the transmitting material is quartz, but other examples of suitable infrared materials include rock salt, germanium, and polyethylene. As shown in FIG. 20, the lens may optionally include a mask of non-transmitting material 85 such that the lens may shape the portion of the beam that is transmitted to the site of irradiation.

The main receptacle 82 is formed by the lens and a wall 88, preferably extending essentially away from the perimeter of the lens. The open end of the main receptacle or rim 90 is placed adjacent to the site of irradiation. The area defined by the lens, wall of the main receptacle and the site of irradiation is thereby substantially enclosed during the operation of the laser perforator device.

The base 86 is the part of the container unit that can optionally be inserted into the applicator. The base may comprise a cylinder, a plurality of prongs or other structure. The base may optionally have threading. Optionally, the base, when fully inserted, disengages a safety mechanism of the laser perforator device, allowing the emission of the laser beam.

Figure 19A:
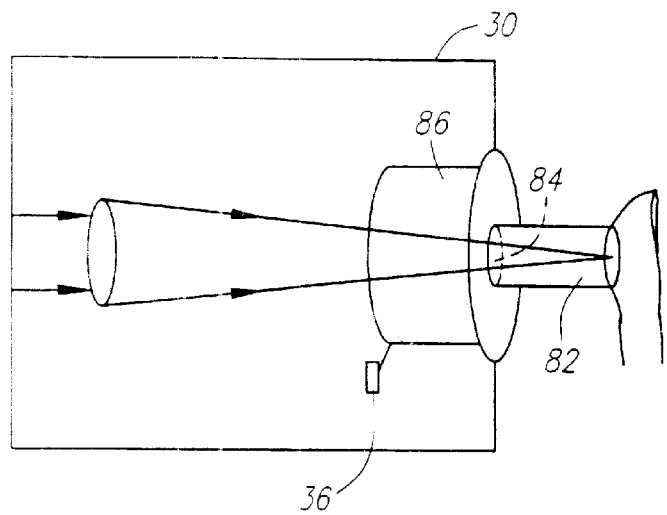
FIG. 19 shows examples of a container unit in use with a laser.
Figure 19B:
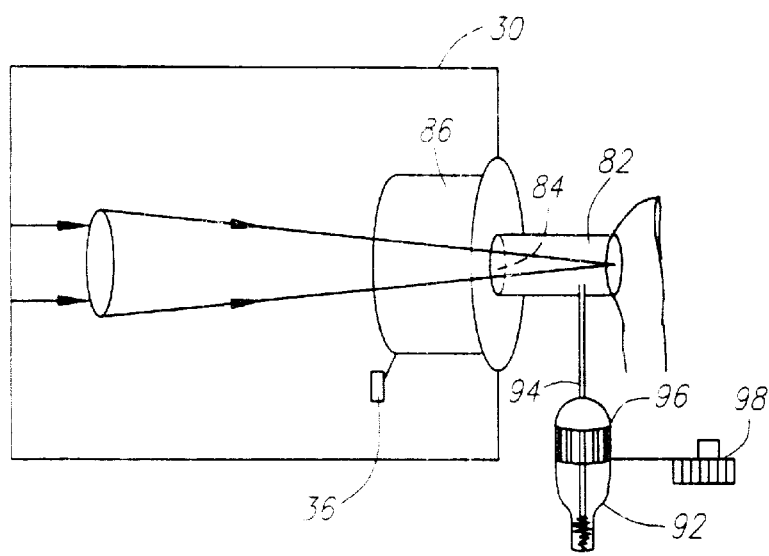

As shown in FIG. 19, the container unit may also include an additional vessel 92 which collects a portion of the matter released as part of irradiation. For example, this vessel can collect interstitial fluid and/or other liquid or particulate matter, while the main receptacle 82 collects the ablated tissue. The interstitial fluid and/or other liquid or particulate matter may be channeled into the vessel through a capillary tube 94 or other tubing which extends from the main receptacle into the vessel. The vessel is optionally detachable. The main receptacle may have a hole 95 in the wall through which the capillary tube or other tubing may be securely inserted. The vessel may have a removable stop 96 which sufficiently covers the open end of the vessel to prevent contamination with undesired material, but has an opening large enough for the capillary tube or other tubing to be inserted. In the preferred embodiment, the capillary tube or other tubing will extend outwardly from the main receptacle's wall and into the vessel through the removable stop. Once the sample has been collected, the stop may optionally be removed and discarded. The vessel may then optionally be sealed with a cap 98 to prevent spillage. The vessel is preferably bullet shaped.

In the first embodiment, the container unit comprises a cylindrical main receptacle 82, a cylindrical base 86, and an at least partially transparent circular lens 84 in the area between the main receptacle and base. Optionally, the lens may include a mask which shapes the beam that perforates the tissue. The container unit is constructed of glass or plastic. The container unit is optionally disposable.

In the second embodiment, the container unit comprises the elements of the first embodiment and also includes an additional vessel 92 and a capillary tube 94 extending outwardly from the main receptacle's wall 88 and into the vessel through a removable stop 96. The vessel may optionally have a cap 98 to seal the opening so as to prevent spillage. The container unit is constructed of glass or plastic. The container unit, including the capillary tube and the additional vessel, are optionally disposable.

FIG. 19 shows examples of the use of the container unit with the laser perforator device. In this embodiment the applicator 30 is surrounded by the housing 34. The container unit is inserted in the applicator 30 and aligned so as to be capable of defeating the interlock 36. The base 86 of the container unit in this embodiment is within the applicator 30, while the rim 90 of the receptacle 82 is located adjacent to the tissue to be perforated. The beam passes through the lens 84.

In a third embodiment, the container unit is evacuated. The optional vacuum in the container unit exerts a less than interstitial fluid or pressure of gases in the blood over the site of irradiation, thereby increasing the efficiency of interstitial fluid collection. The container unit's end proximal to the site of irradiation is optionally sealed air-tight with a plug 70. The plug is constructed of material of suitable flexibility to conform to the contours of the site of irradiation (e.g., the finger). The desired site of irradiation is firmly pressed against the plug. The plug's material is impermeable to gas transfer. Furthermore, the plug's material is thin enough to permit perforation of the material as well as irradiation of the skin by the laser. In the preferred embodiment, the plug is constructed of rubber.

Figure 9:
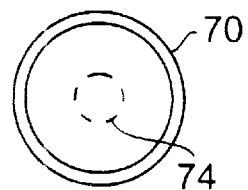
FIG. 9 shows a plug and plug perforation center.

The plug perforation center 74, as shown in FIG. 9, is preferably constructed of a thin rubber material. The thickness of the plug is such that the plug can maintain the vacuum prior to perforation, and the laser can perforate the plug and irradiate the tissue adjacent to the plug. For use with an Er:YAG laser, the plug should be in the range of approximately 100 to 500 microns thick, but at the most 1 millimeter thick.

The plug perforation center 74 is large enough to cover the site of irradiation. Optionally, the perforated site is a round hole with an approximate diameter ranging from 0.1–1 mm, or slit shaped with an approximate width of 0.05–0.5 mm and an approximate length up to 2.5 mm. Thus, the plug perforation center is sufficiently large to cover irradiation sites of these sizes.

The site of irradiation is firmly pressed against the rubber material. Optionally, an annular ring of adhesive can be placed on the rubber plug to provide an air-tight seal between the site of irradiation and the container unit. Preferably the perforation site on the plug is stretched when the tissue is pressed against the plug. This stretching of the plug material causes the hole created in the plug to expand beyond the size of the hole created in the tissue. As a result, the interstitial fluid can flow unimpeded into the container unit 68. The laser beam penetrates the container unit, perforates the plug perforation center 74 and irradiates the patient's tissue.

Figure 10:
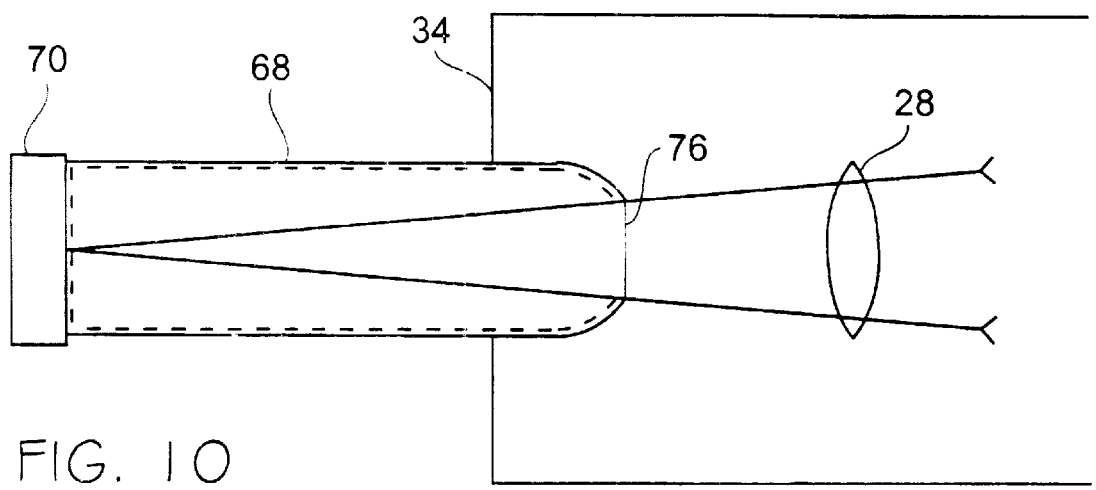
FIG. 10 shows an optional container unit for collecting ablated tissue and reducing noise resulting from the interaction between the laser and the patient's tissue.

In a fourth embodiment of the container unit, as shown in FIG. 10, the container unit 68 includes a hole 76 through which the laser passes. In this fourth embodiment, the container unit optionally solely collects ablated tissue. As in the other embodiments, the site of irradiation is firmly pressed against the container unit. The container unit can optionally include a plug proximal to the site of irradiation, however it is not essential because there is no need to maintain a vacuum in this embodiment. All embodiments of the container unit reduce the noise created from interaction between the laser beam and the patient's tissue and thus alleviate the patient's anxiety and stress.

Figure 18:
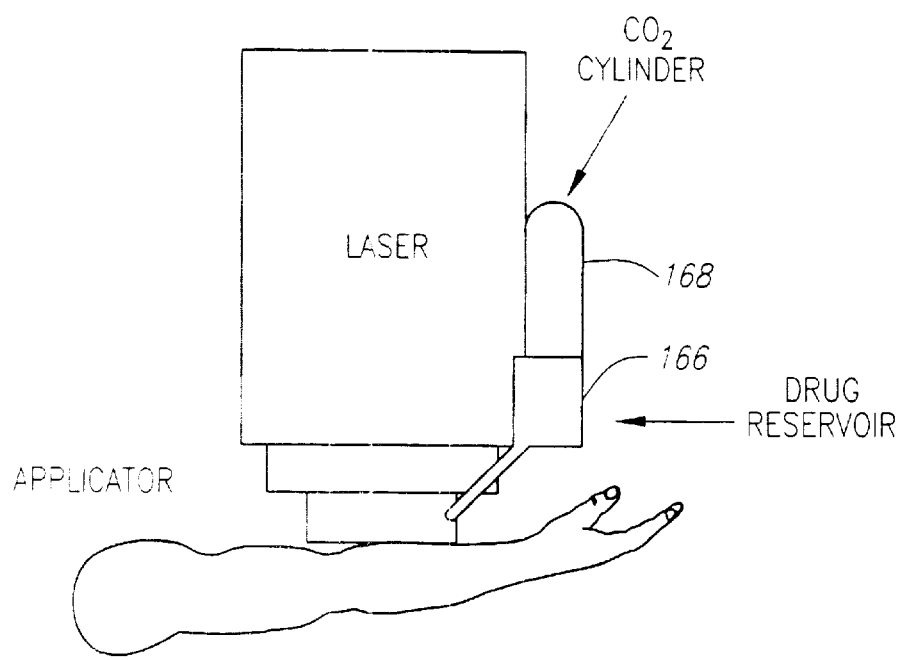
FIG. 18 shows an atomizer for the delivery of pharmaceuticals.

The container may also be modified to hold, or receive through an opening, a pharmaceutical or other substance, which may then be delivered shortly after testing of interstitial fluid. FIG. 11 shows an example of a container with a built-in drug reservoir and roll-on apparatus for delivery. FIG. 18 shows a container with an applicator which in turn comprises an atomizer with attached high pressure gas cylinder.

Optionally, the container unit is disposable, so that the container unit and plug can be discarded after use. Additionally, the main receptacle of the container unit, capillary tube and/or additional vessel can contain reagents for various tests to be performed on the collected interstitial fluid, such as the glucose oxidase test described above. The reagents are positioned so that they will not be in the pathway of the laser light. The reagents are preferably present in a dry form, coating the interior walls of the collection part of the container unit, and thus readily available for interaction with the interstitial fluid sample as it is collected.

Figure 39:
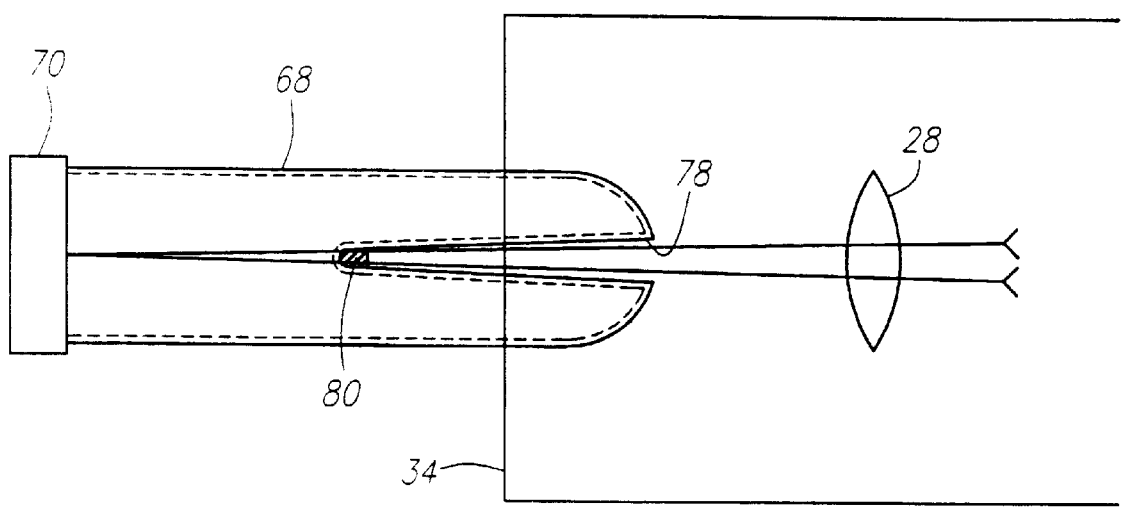
FIG. 39 shows an optional version of the collection container unit that is especially useful when the container unit includes a reagent for mixing with the sample.

A preferable configuration for the container unit when it contains a regent is shown in FIG. 39. In this configuration, the container unit has an indentation 78 at the base such that any fluid reagent present in the container unit will not fall into the line of fire of the laser beam when the container unit is held either vertically or horizontally. The apex 80 of the indented are is made of an infrared-transparent substance, such as quartz, or a near transparent substance.

When reagents are present in the container unit prior to collection of the interstitial fluid sample, it is beneficial to label the container unit in some manner as to the reagents contained inside, or as to the test to be performed on the sample using those reagents. A preferred method for such labelling is through the use of color-coded plugs. For example, a blue plug might indicate the presence of reagent A, while a red plug might indicate the presence of reagents B plus C within the container unit.

Modulated Laser

In addition to the pulsed lasers listed above, a modulated laser can be used to duplicate a pulsed laser for the purpose of enhancing topical drug delivery, as well as enhancing the removal of fluids. This is accomplished by chopping the output of the continuous-wave laser by either modulating the laser output mechanically, optically or by other means such as a saturable absorber. (See, e.g., Jeff Hecht, The Laser Guidebook, McGraw-Hill:NY, 1992). Examples of continuous-wave lasers include $CO_2$, which lases over a range between 9–11 microns (e.g. Edinburgh Instruments, Edinburgh, UK), Nd:YAG, Thallium:YAG (Tm:YAG), which lases at 2.1 microns (e.g. CLR Photonics Inc., Boulder Colo.), semiconductor (diode) lasers which lase over a range from 1.0–2.0 microns (SDL Inc., San Jose, Calif.).

The chopping of the laser output (for example, with a mechanical chopper from Stanford Research Instruments Inc., Sunnyvale Calif.) will preferably result in discrete moments of irradiation with temporal widths from a few tenths of milliseconds, down to nanoseconds or picoseconds. Alternatively, in the case of diode lasers, the lasing process can be modulated by modulating the laser excitation current. A modulator for a laser diode power supply can be purchased from SDL Inc., San Jose, Calif. Alternatively, the continuous-wave beam can be optically modulated using, for example, an electro-optic cell (e.g. from New Focus Inc., Santa Clara, Calif.) or with a scanning mirror from General Scanning, Inc., Watertown Mass.

The additive effect of multiple perforations or alterations may be exploited with diode lasers. Laser diodes supplied by SDL Corporation (San Jose, Calif.) transmit a continuous beam of from 1.8 to 1.96 micron wavelength radiant energy. These diodes operate at up to 500 mW output power and may be coupled to cumulatively produce higher energies useful for stratum corneum ablation. For example, one diode bar may contain ten such diodes coupled to produce pulsed energy of 5 mJ per millisecond. It has been shown that an ablative effect may be seen with as little as 25 mJ of energy delivered to a 1 mm diameter spot. Five (5) millisecond pulses or (25) one millisecond pulses from a diode laser of this type will thus have an ablative effect approximately equivalent to one 25 mJ pulse in the same time period.

The following examples are descriptions of the use of a laser to increase the permeability of the stratum corneum for the purpose of drawing fluids, as well as for pharmaceutical delivery. These examples are not meant to limit the scope of the invention, but are merely embodiments.

EXAMPLE 1

The laser comprises a flashlamp (PSC Lamps, Webster, N.Y.), an Er:YAG crystal (Union Carbide Crystal Products, Washagoul, Wash.), optical-resonator mirrors (CVI Laser Corp., Albuquerque, N.Mex.), an infrared transmitting lens (Esco Products Inc., Oak Ridge, N.J.), as well as numerous standard electrical components such as capacitors, resistors, inductors, transistors, diodes, silicon-controlled rectifiers, fuses and switches, which can be purchased from any electrical component supply firm, such as Newark Electronics, Little Rock, Ariz.

EXAMPLE 2

An infrared laser radiation pulse was formed using a solid state, pulsed, Er:YAG laser consisting of two flat resonator mirrors, an Er:YAG crystal as an active medium, a power supply, and a means of focusing the laser beam. The wavelength of the laser beam was 2.94 microns. Single pulses were used.

The operating parameters were as follows: The energy per pulse was 40, 80 or 120 mJ, with the size of the beam at the focal point being 2 mm, creating an energy fluence of 1.27, 2.55 or 3.82 $J/cm^2$. The pulse temporal width was 300 $\mu s$, creating an energy fluence rate of 0.42, 0.85 or $1.27\times10^4$ $W/cm^2$.

Transepidermal water loss (TEWL) measurements were taken of the volar aspect of the forearms of human volunteers. Subsequently the forearms were positioned at the focal point of the laser, and the laser was discharged. Subsequent TEWL measurements were collected from the irradiation sites, and from these the measurements of unirradiated controls were subtracted. The results (shown in FIG. 27) show that at pulse energies of 40, 80 and 120 mJ, the barrier function of the stratum corneum was reduced and the resulting water loss was measured to be 131, 892 and 1743 $gm/m^2/hr$ respectively. The tape stripe positive control (25 pieces of Scotch Transpore tape serially applied and quickly removed from a patch of skin) was measured to be 9.0 $gm/m^2/hr$, greater than untouched controls; thus the laser is more efficient at reducing the barrier function of the stratum corneum than tape-stripping.

Clinical assessment was conducted 24 hours after irradiation. Only a small eschar was apparent on the site lased at high energy, and no edema was present. None of the volunteers experienced irritation or required medical treatment.

EXAMPLE 3

An infrared laser radiation pulse was formed using a solid state, pulsed, Er:YAG laser consisting of two flat resonator mirrors, an Er:YAG crystal as an active medium, a power supply, and a means of focusing the laser beam. The wavelength of the laser beam was 2.94 microns. A single pulse was used.

The operating parameters were as follows: The energy per pulse was 60 mJ, with the size of the beam at the focal point being 2 mm, creating an energy fluence of 1.91 J/cm$^2$. The pulse temporal width was 300 $\mu$s, creating an energy fluence rate of 0.64×10$^4$ W/cm$^2$.

The volar aspect of the forearm of a volunteer was placed at the focal point of the laser, and the laser was discharged. After discharge of the laser, the ablated site was topically administered a 30% liquid lidocaine solution for two minutes. A 26G-0.5 needle was subsequently inserted into the laser ablated site with no observable pain. Additionally, after a 6 minute anesthetic treatment, a 22G-1 needle was fully inserted into the laser ablated site with no observable pain. The volunteer experienced no irritation and did not require medical treatment.

EXAMPLE 4

Ablation threshold energy: Normally hydrated (66%) stratum corneum was sandwiched between two microscope cover slides, and exposed to a single pulse of irradiation from the Er:YAG laser. Evidence of ablation was determined by holding the sample up to a light and seeing whether any stratum corneum was left at the irradiated site. From this experiment, it was determined that the irradiation threshold energy (for a 2 mm irradiation spot) was approximately 90–120 mJ. The threshold will likely be higher when the stratum corneum is still overlying epidermis, as in normal skin, since it takes energy to remove the stratum corneum from the epidermis, to which it is adherent.

EXAMPLE 5

Figure 28:
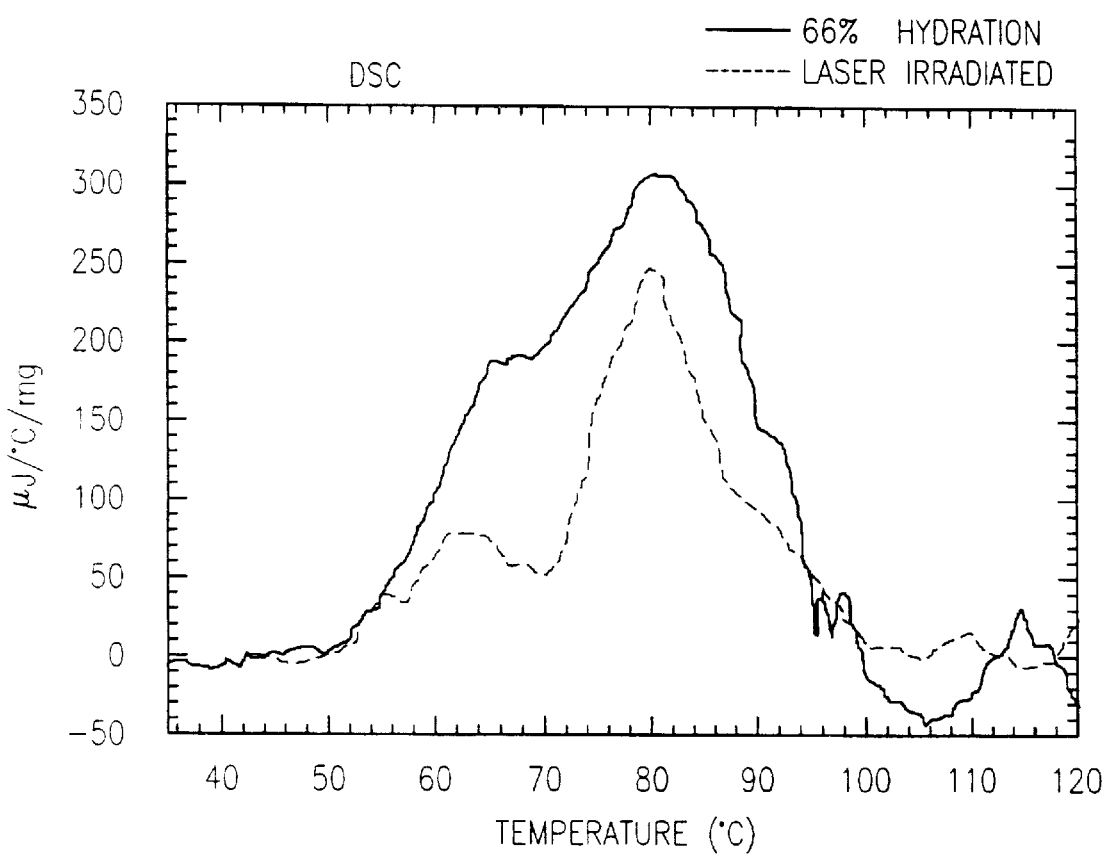
FIG. 28 is a chart showing a DSC scan of normally hydrated (66%) human stratum corneum, and a scan of Er:YAG laser irradiated stratum corneum using a subablative pulse energy of 60 mJ.
Figure 29:
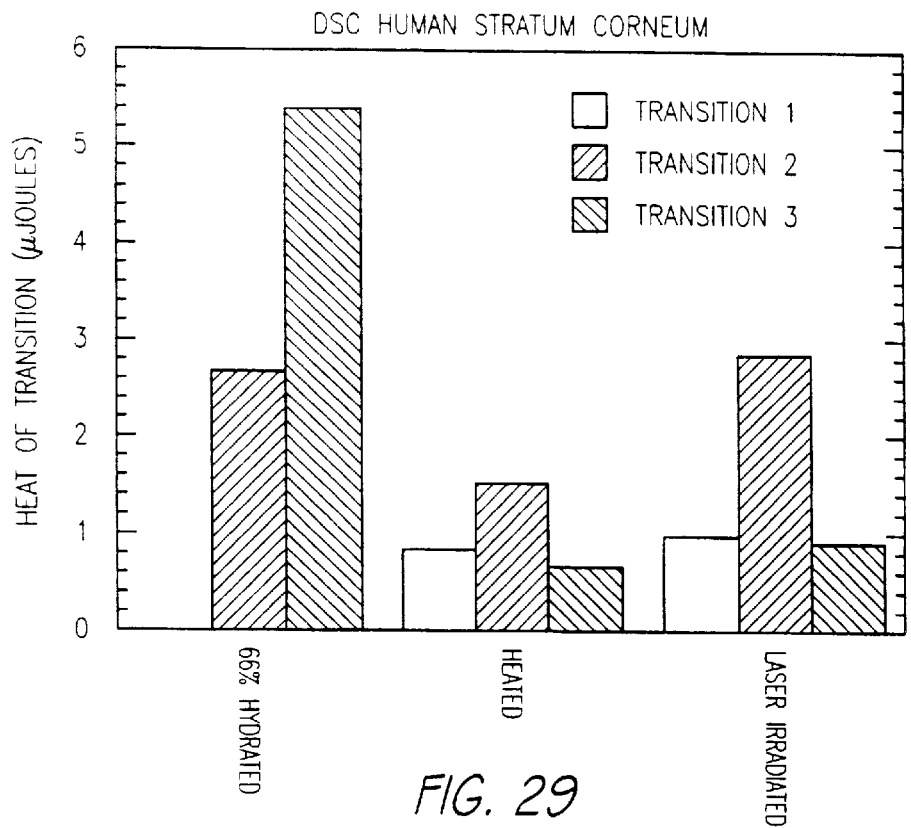
FIGS. 29–31 are charts showing the heat of transition ($\mu$J), center of the transition (° C.) and the full-width at half-maximum of the transition (° C.) of three peaks in the DSC spectra of stratum corneum treated different ways.
Figure 30:
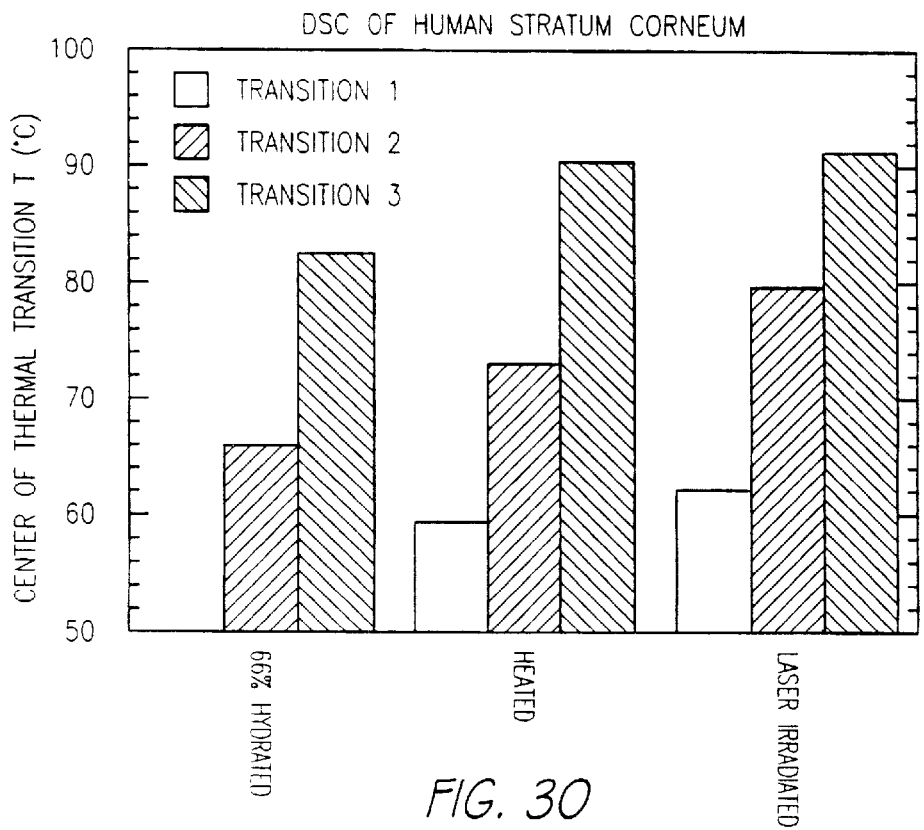
Figure 31:
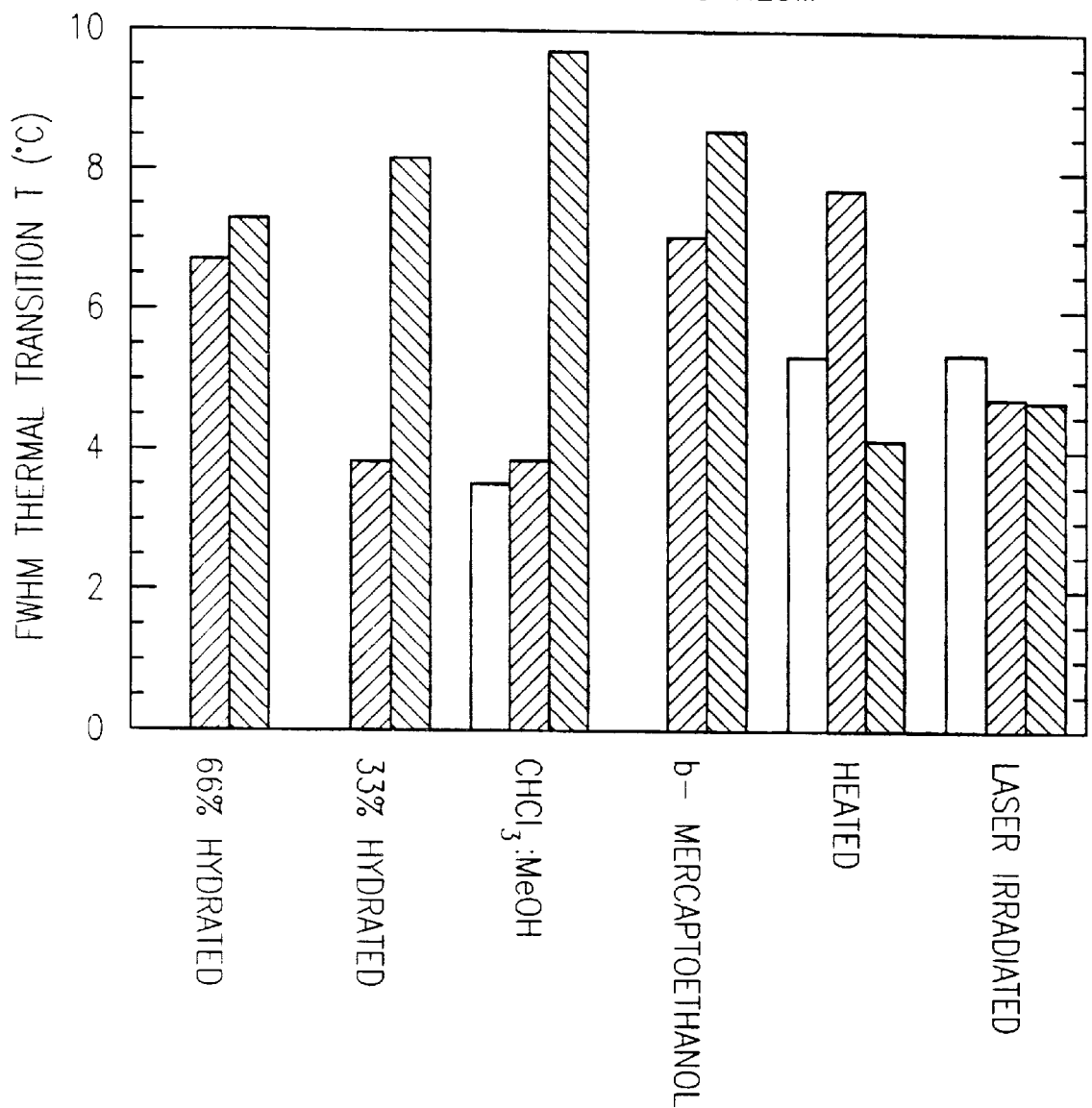

Differential Scanning Calorimetry (DSQ: FIG. 28 shows a DSC scan of normally hydrated (66%) human stratum corneum, and a scan of stratum corneum irradiated with the Er:YAG laser using a subablative pulse energy of 60 mJ. Defining the thermal transition peaks at approximately 65, 80 and 92° C., we determined the heat of transition ($\mu$J), center of the transition (° C.) and the full-width at half-maximum of the transition (° C.) (FIGS. 29–31). The results shown are on normal 66% hydrated stratum corneum, dehydrated 33% stratum corneum, steam heated stratum corneum, Er:YAG laser irradiated stratum corneum, or stratum corneum that was immersed in chloroform-methanol (a lipid solvent), or beta-mercaptoethanol (a protein denaturant). The effect of laser irradiation on stratum corneum is consistent (depending on which transition you look at, 1, 2 or 3) with changes seen due to thermal damage (i.e. heated with steam), and delipidization. Permeation with ($^3$H$_2$0) and transepidermal impedance experiments on skin treated the same way showed that the-result of these treatments (heat, solvent or denaturant) resulted in increased permeation. Thus, the changes induced in the stratum corneum with these treatments, changes which are consistent with those seen in laser irradiated stratum corneum, and changes which do not result in stratum corneum ablation, result in increased permeation.

EXAMPLE 6

Figure 32:
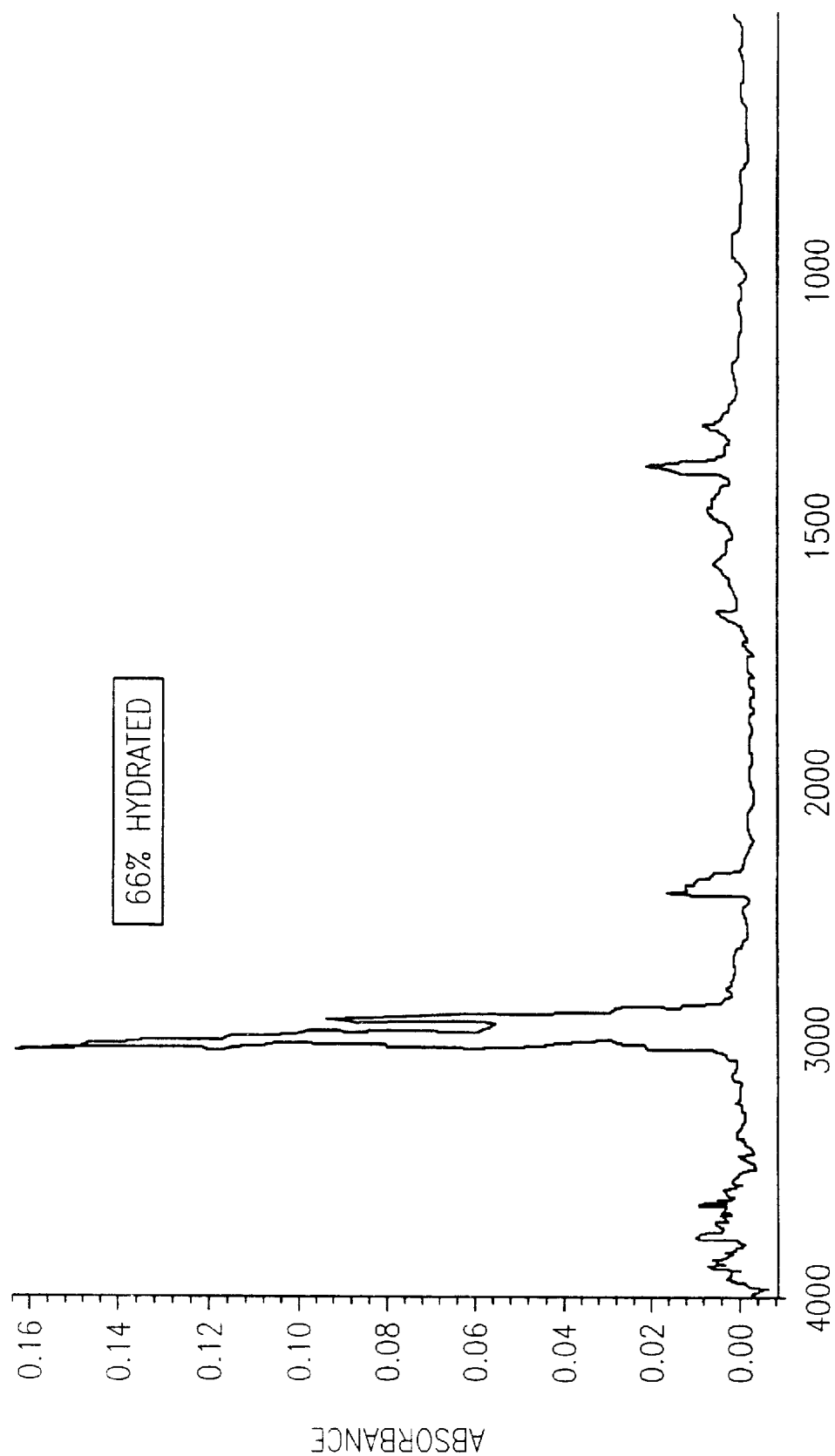
FIGS. 32–33 are charts of FRIR spectra of control and lased stratum corneum.
Figure 33:
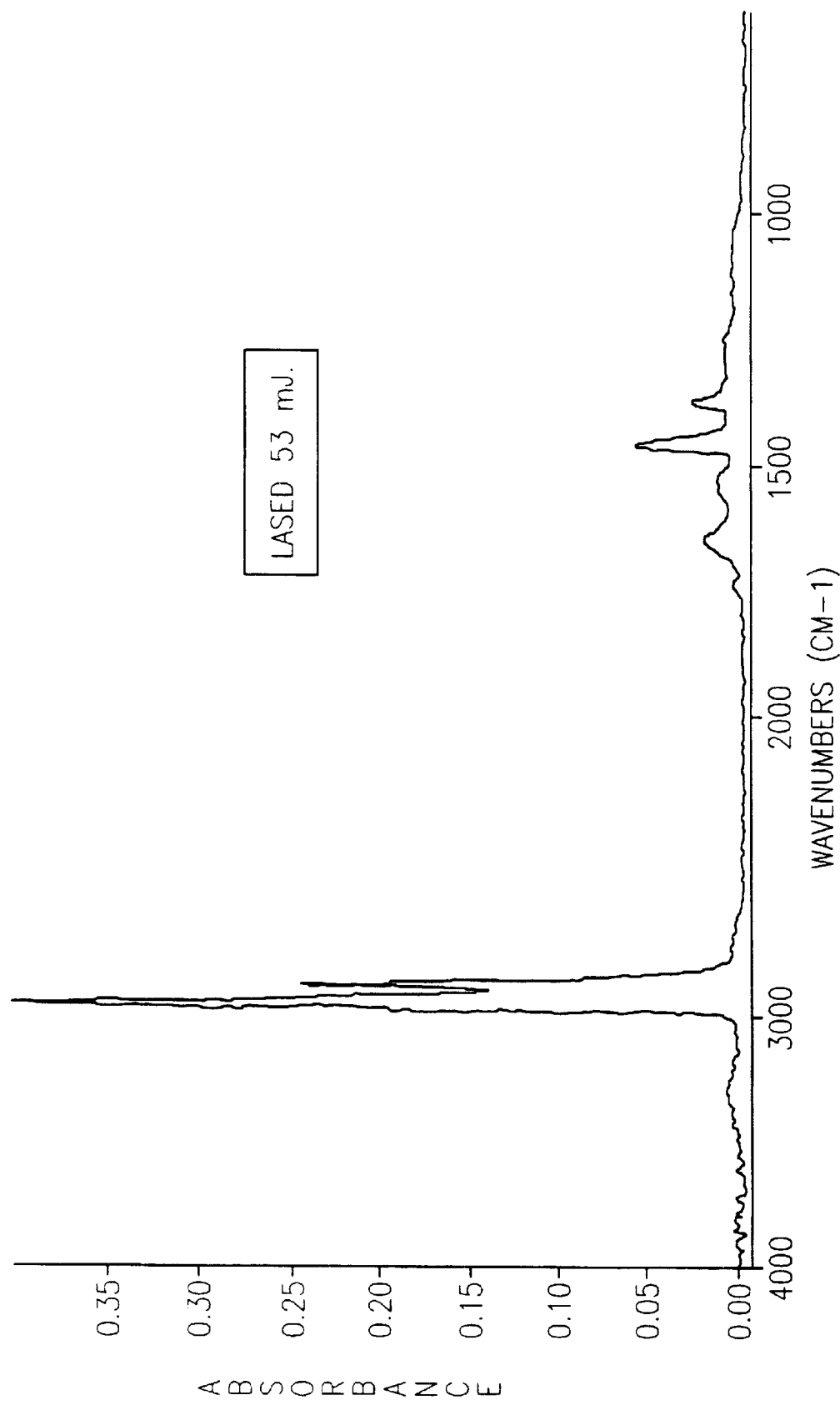
Figure 34:
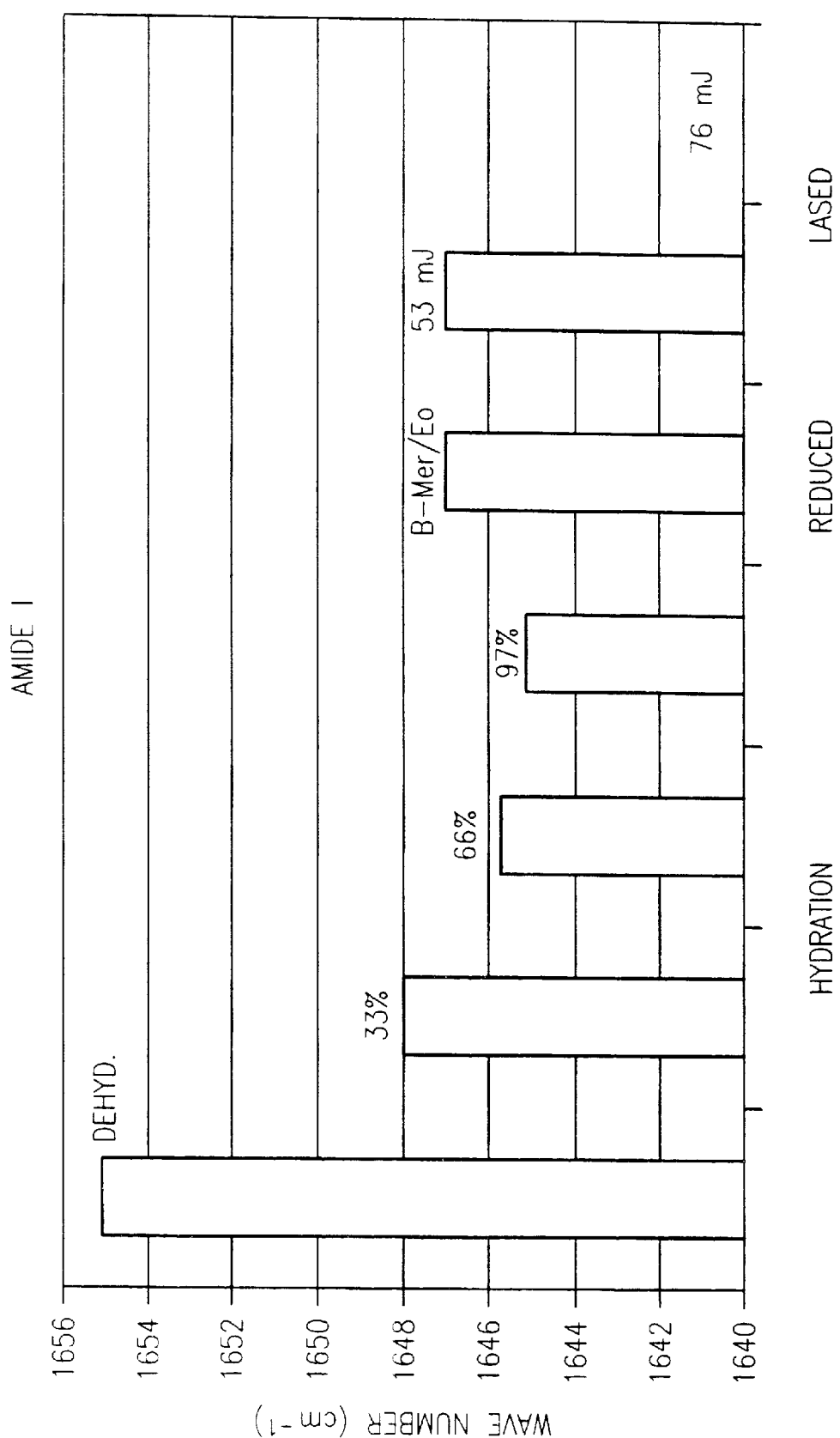
FIG. 34 shows Amide I band position ($cm^{-1}$) as a function of stratum corneum treatment.
Figure 35:
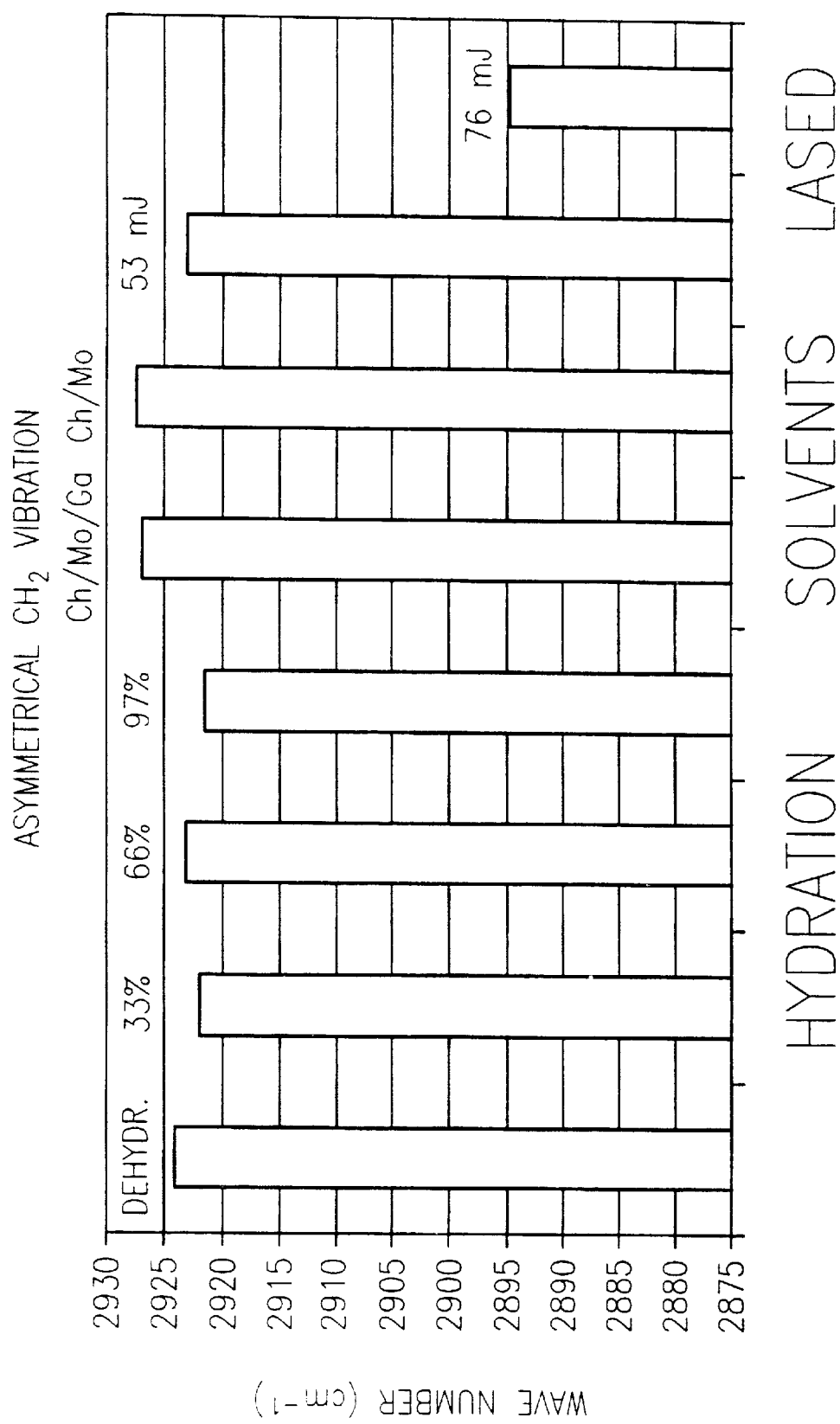
FIG. 35 shows $CH_2$ vibration position ($cm^{-1}$) as a function of stratum corneum treatment.

Fourier Transform Infrared (FTIR) Spectroscopy: FTIR spectroscopy was used to study stratum corneum treated the same way as in the above DSC experiments, except the energy used was between 53 and 76 mJ. The spectra (see, e.g., FIGS. 32–33) show that absorption bands that are due to water, proteins and lipids change when the stratum corneum is irradiated. Some of these changes are consistent with changes seen during non-laser treatment of the stratum corneum (e.g. desiccation, thermal damage, lipid solubilization, or protein denaturation). For example, the Amide I and II bands, which are due to the presence of proteins (most likely keratin, which makes up the bulk of protein in stratum corneum), shift to a larger wavenumber, consistent with the effect of desiccation alone (in the case of Amide II) or desiccation and beta-mercaptoethanol treatment (in the case of Amide I) (see, e.g., FIG. 34). The CH$_2$ vibrations (due to bonds in lipids) always shift to a smaller wavenumber indicating that either the intermolecular association between adjacent lipid molecules has been disturbed and/or the environment around the lipid molecules has changed in such a way that the vibrational behavior of the molecules changes (see, e.g., FIG. 35).

EXAMPLE 7

Figure 36:
FIG. 36 shows a histological section of rat skin that was irradiated at 80 mJ.
Figure 37:
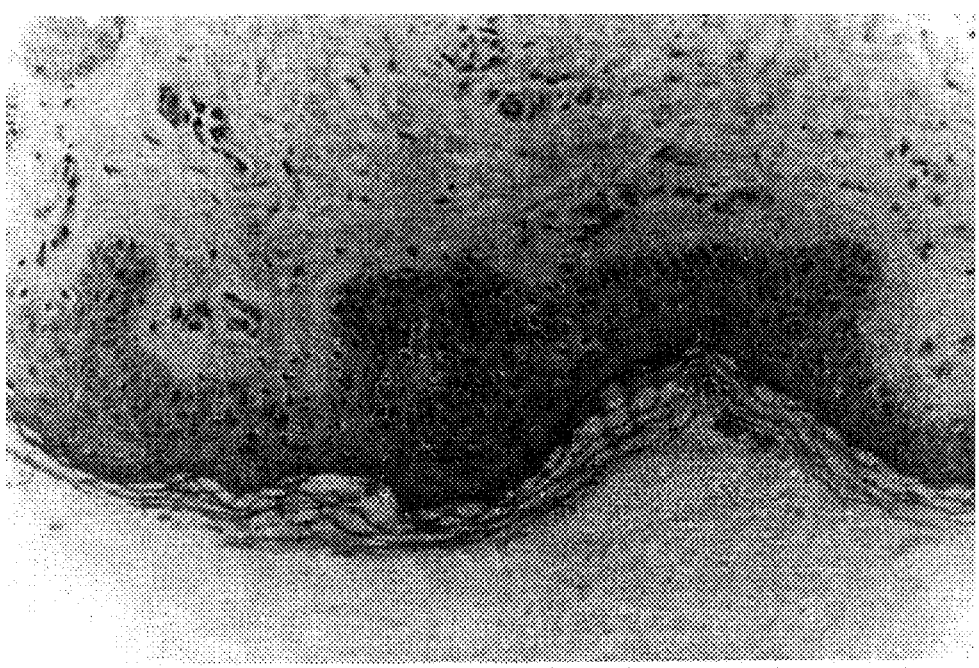
FIG. 37 shows a histological section of human skin that was irradiated at 80 mJ.

Histology: Numerous in vivo experiments have been done on rats and humans. Usually, the skin is irradiated with the Er:YAG laser and a 2 mm spot and with a particular pulse energy, and then the irradiated site is biopsied immediately or 24 hours later. Two examples of typical results are shown in FIGS. 36 and 37. FIG. 36 shows rat skin irradiated at 80 mJ, which is an energy sufficient to make the skin permeable (to lidocaine, for instance) and yet does not show any sign of stratum corneum ablation. FIG. 37 depicts human skin 24 hours after being irradiated at 80 mJ. In this case, some change in the appearance of the stratum corneum has taken place (perhaps coagulation of some layers of stratum corneum into a darkly staining single layer), and yet the stratum corneum is still largely intact and is not ablated. Irradiation of human skin, in vivo, and subsequent examination under a dissection microscope, show that at subablative energies (less than about 90–120 mJ), the stratum corneum is still present on the skin. The irradiated stratum corneum appears slightly whitened in vivo, which might be evidence of desiccation or separation of the stratum corneum from the underlying tissue.

EXAMPLE 8

Figure 22:
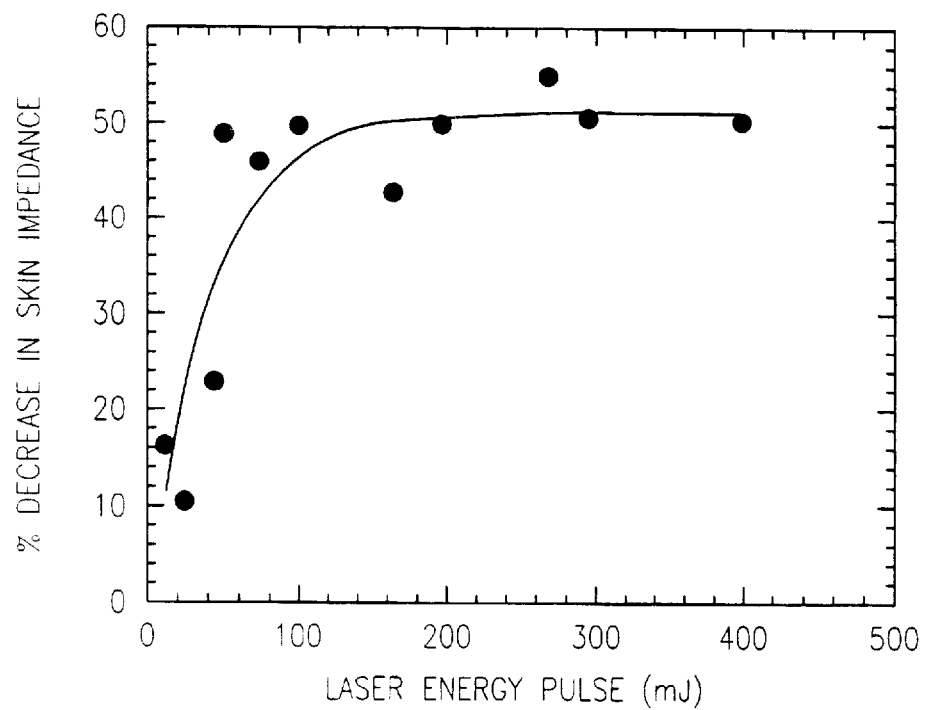
FIG. 22 shows the decrease in the impedance of skin using various laser pulse energies.

One way to quantify the reduction in the barrier function of the stratum corneum is to measure the reduction in the electrical impedance of the skin as a consequence of laser irradiation. In this experiment, separate 2 mm spots on the volar aspect of the forearm of a human volunteer were irradiated with a single pulse of radiant energy from the Er:YAG laser using a range of energies. An ECG electrode was then placed over the irradiated site and an unirradiated site about 20 cm away on the same forearm. A 100 Hz sine wave of magnitude 1 volt peak-to-peak was then used to measure the impedance of the skin. The results of a series of measurements are shown in FIG. 22, which shows that there is a decrease in skin impedance in skin irradiated at energies as low as 10 mJ, using the fitted curve to interpolate data.

EXAMPLE 9

Figure 21:
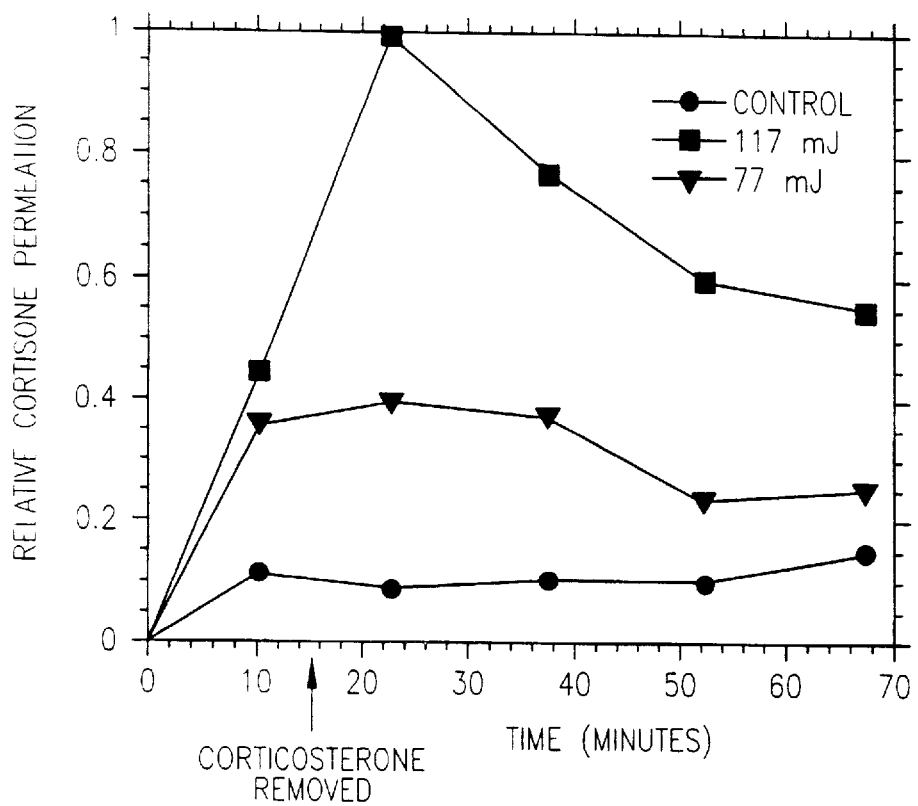
FIG. 21 is a chart showing a study using corticosterone which showed enhanced permeation through skin irradiated at an energies of 77 mJ and 117 mJ.
Figure 26:
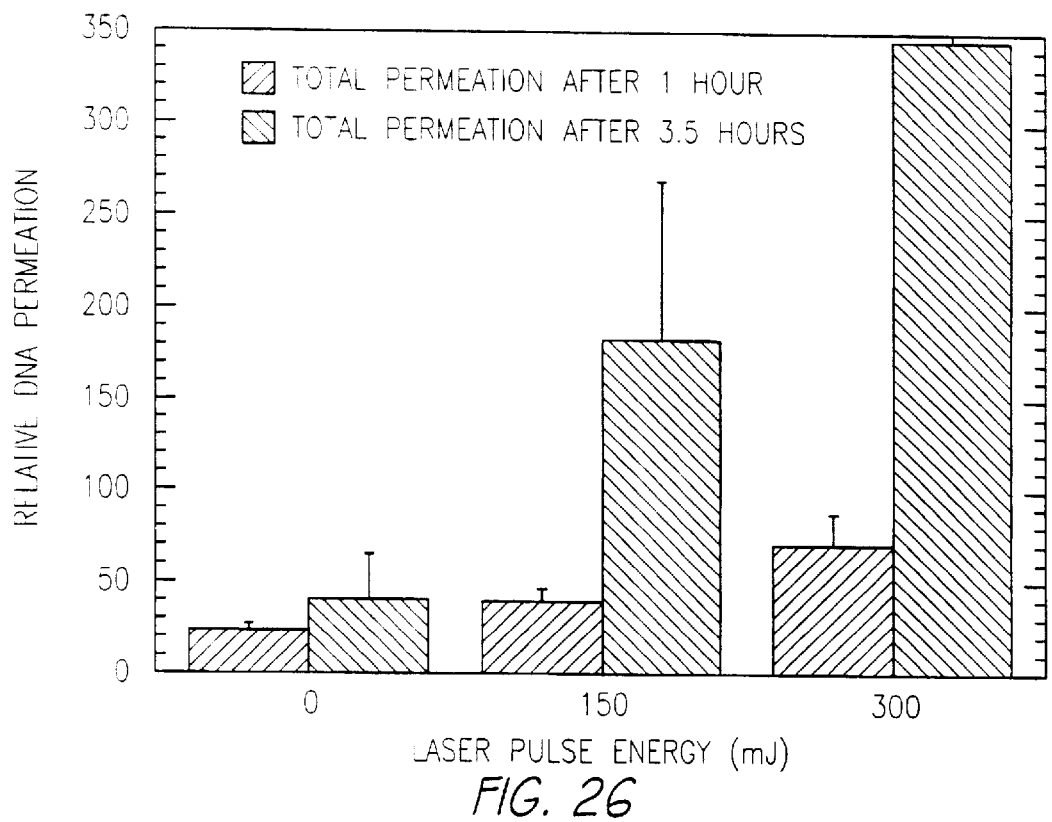
FIG. 26 is a chart of a study using DNA showing enhanced permeation through skin irradiated at an energy of 150 mJ and 300 mJ.

Pieces of human skin were placed in diffusion cells and irradiated with a single pulse of radiant energy produced by an Er:YAG laser. The spot size was 2 mm and the energy of the pulse was measured with a calibrated energy meter. After irradiation, the diffusion cells were placed in a 37 degrees Celsius heating block. Phosphate buffered saline was added to the receptor chamber below the skin and a small stir bar was inserted in the receptor chamber to keep the fluid continually mixed. Control skin was left unirradiated. Small volumes of radiolabelled compounds (either corticosterone or DNA) were then added to the donor chamber and left for 15 minutes before being removed (in the case of corticosterone) or were left for the entire duration of the experiment (in the case of the DNA). Samples were then taken from the receptor chamber at various times after application of the test compound and measured in a scintillation or gamma counter. The results of this experiment are shown in FIGS. 21 and 26. The results illustrate that enhanced permeation can occur at sub-ablative laser pulse energies (see the 77 mJ/pulse data for corticosterone). Although, in the case of the DNA experiment the energy used may have been ablative, enhanced permeation may still occur when lower energies are used.

EXAMPLE 10

Figure 23:
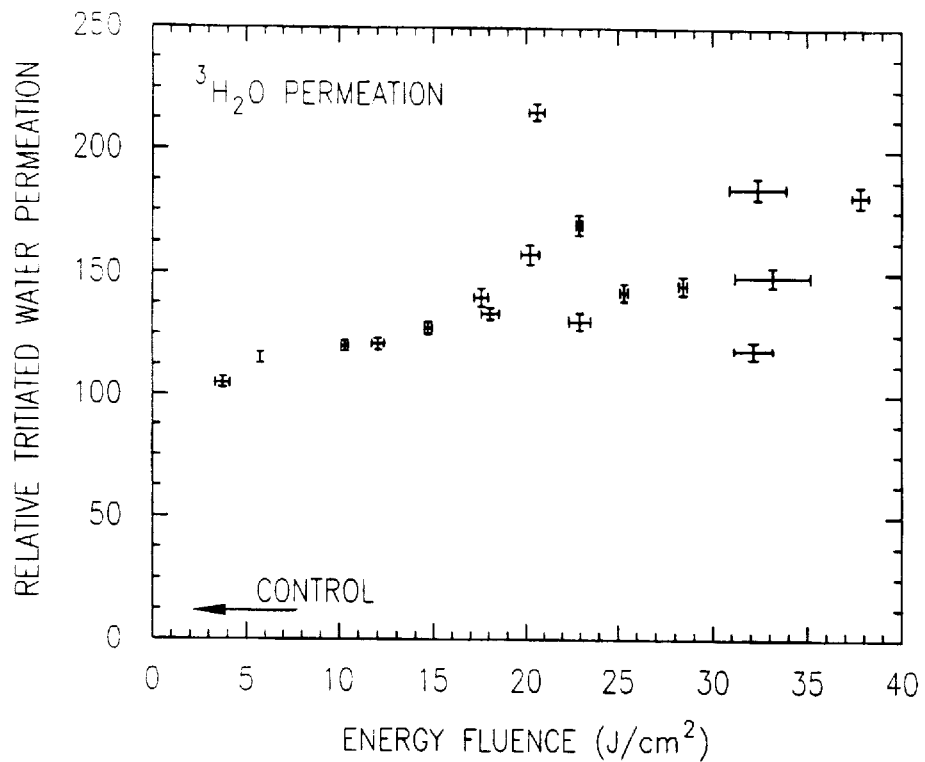
FIGS. 23–24 show in a permeation study of tritiated water ($^3H_2O$) involving lased human skin at energies from 50 mJ (1.6 J/cm$^2$) to 1250 mJ (40 J/cm$^2$).
Figure 24:
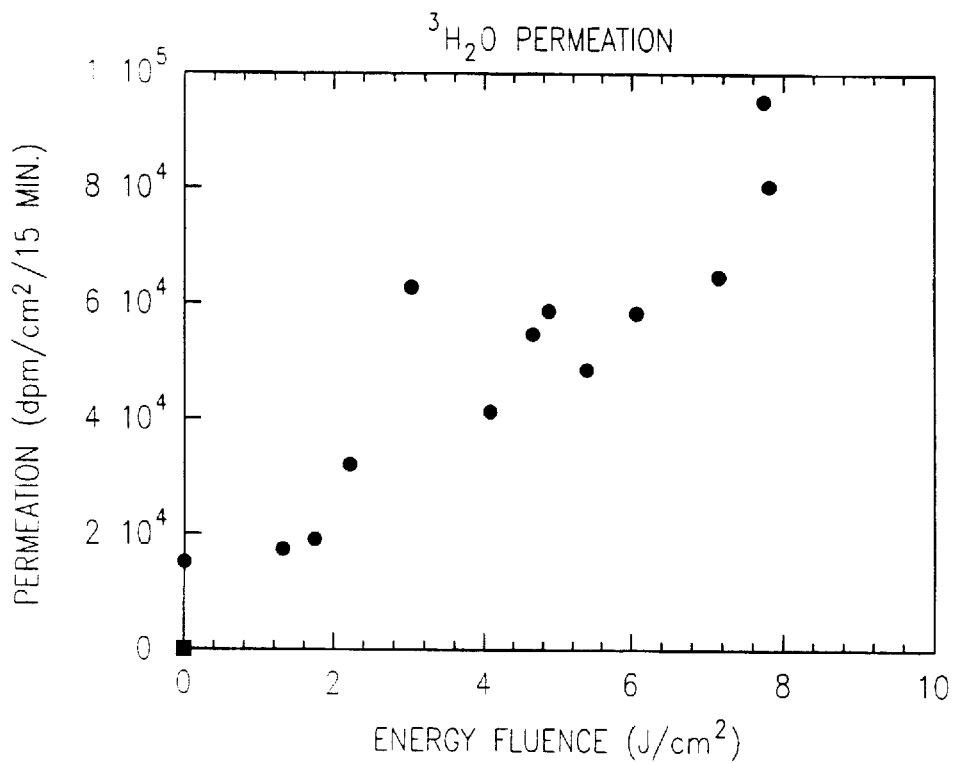
Figure 25A:
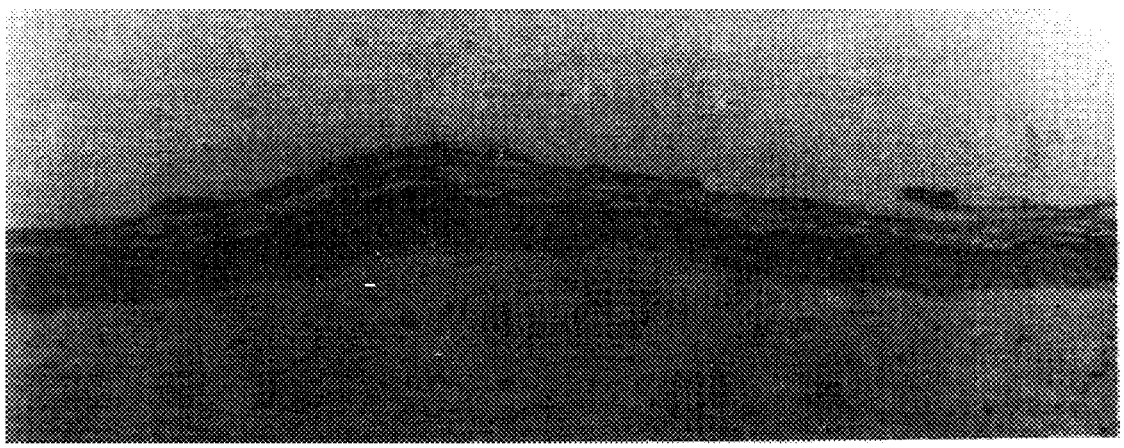
FIG. 25 shows histological sections of human skin irradiated at energies of 50 mJ and 80 mJ.
Figure 25B:
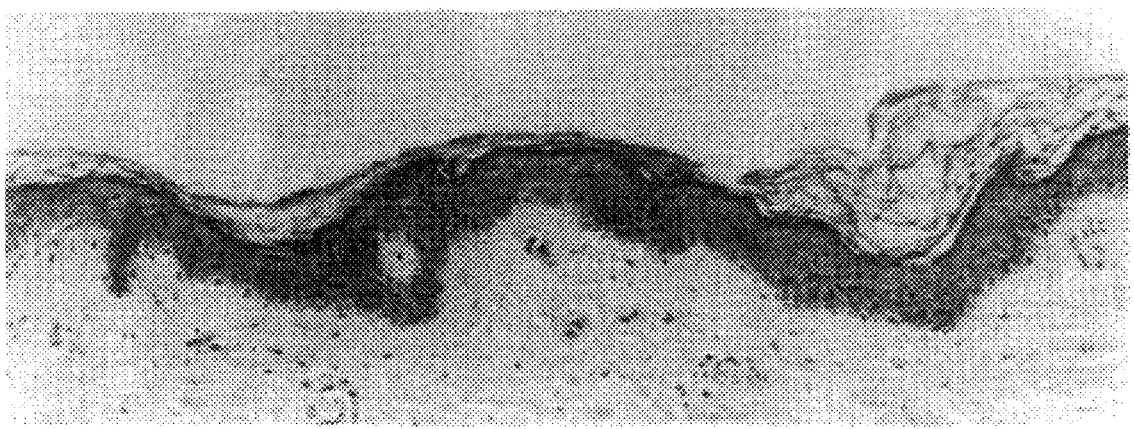

Histology studies on rat and human skin, irradiated either in vivo or in vitro, show little or no evidence of ablation when Er:YAG laser pulse energies less than about 100–200 mJ are used. (See, e.g., FIG. 25). Repeating this study showed the same results as the previous studies. An in vitro permeation study using tritiated water ($^3H_2O$) involving human skin lased at energies from 50 mJ (1.6 J/cm$^2$) to 1250 mJ (40 J/cm$^2$) determined (FIGS. 23 and 24) that an increase in permeation was seen at low energy fluences up to about 5 J/cm$^2$, whereupon the permeation is more-or-less constant. This shows that there has been a lased induced enhancement of permeation (of tritiated water) at energies that are sub-ablative.

EXAMPLE 11

Figure 40:
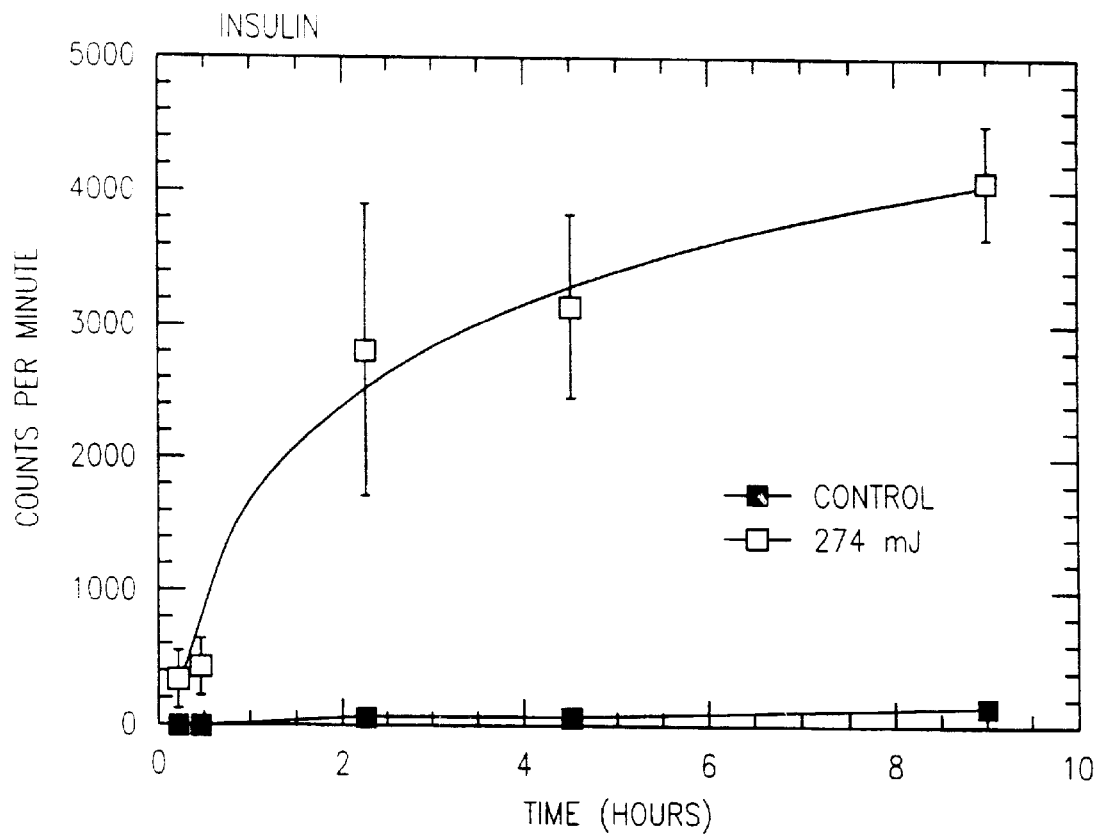
FIG. 40 shows permeation of insulin through human skin in vitro.

The output of the Er:YAG laser was passed through an aperture to define it's diameter as 2 mm. Human skin, purchased from a skin bank, was positioned in Franz diffusion cells. The receptor chamber of the cell was filled with 0.9% buffered saline. A single pulse, of measured energy, was used to irradiate the skin in separate diffusion cells. Control skin was left unirradiated. In the case of insulin, a 274 mJ pulse was used, and multiple samples were irradiated. After irradiation, a stirring magnet was place in the receptor chamber of the diffusion cells and the cells were placed in a heating block held at 37 EC. The radiolabelled insulin was diluted in buffered saline, and 100 µL of the resulting solutions was placed in the donor chamber of separate diffusion cells. The donor was left on the skin for the duration of the experiment. At various times post-drug-application, samples were taken from the receptor chamber and the amount of drug present was assayed with either a gammacounter, or a liquid scintillation counter. A graph of the resulting data is shown in FIG. 40. From this, and similar data, the permeability constant ($K_p$) for insulin was derived to be 11.3+/−0.93 (×10$^{-3}$ cm/hr).

EXAMPLE 12

Figure 27:
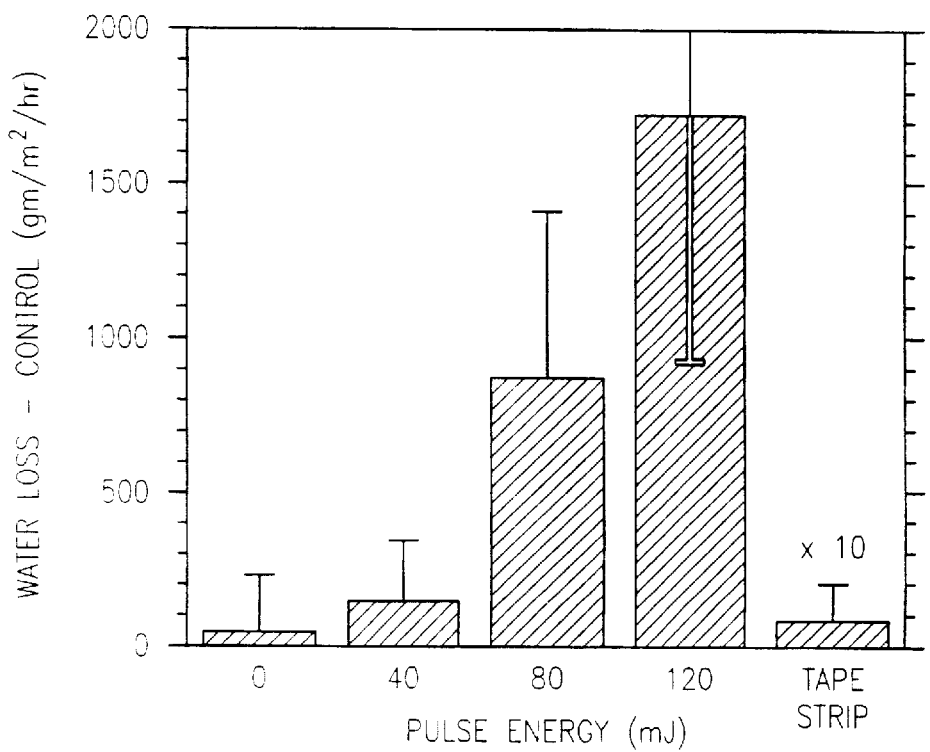
FIG. 27 shows laser pulse energy (J) versus water loss through human skin in vivo.
Figure 38A:
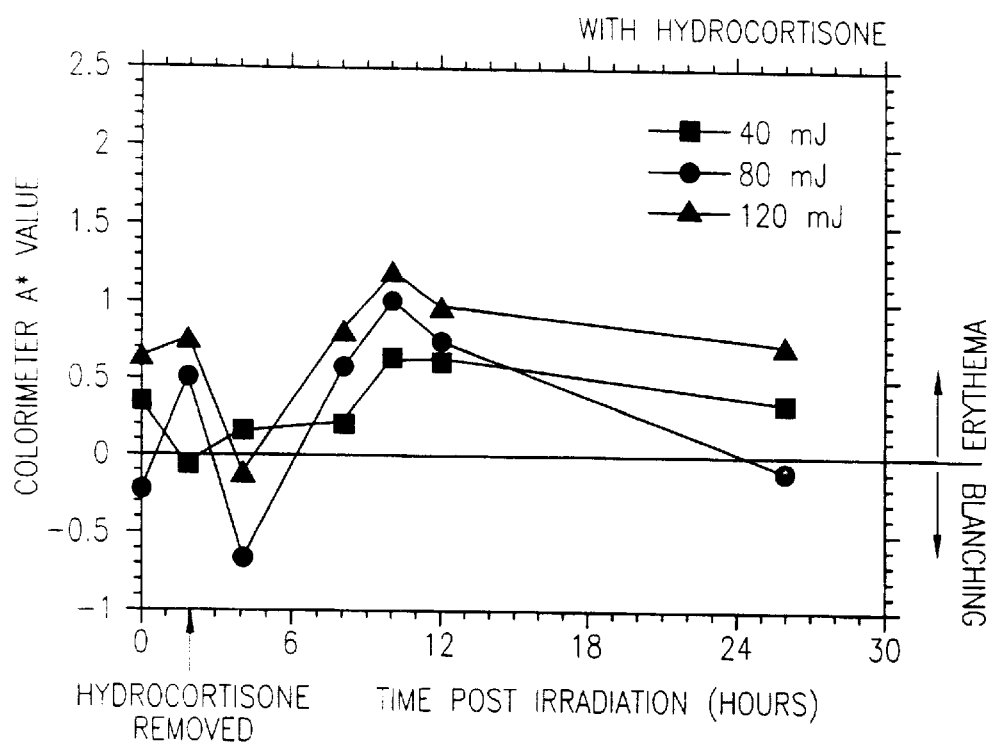
FIG. 38 shows in vivo blanching assay results.
Figure 38B:
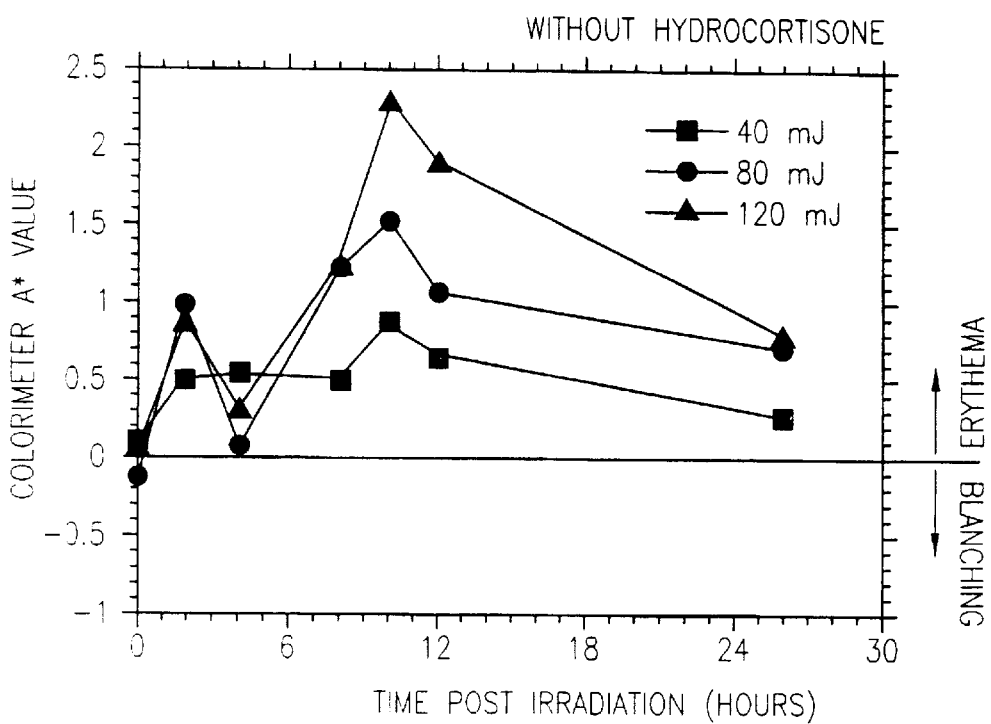

This data was collected during the same experiment as the TEWL results (see Example 2 and FIG. 27). In the case of the blanching assay, baseline skin color (redness) measurements were then taken of each spot using a Minolta CR-300 Chromameter (Minolta Inc., N.J.). The Er:YAG laser was then used to ablate six 2 mm spots on one forearm, at energies of 40, 80 and 120 mJ. A spot (negative calorimeter control) directly adjacent to the laser irradiated spots remained untouched. Subsequently, a thin film of 1% hydrocortisone ointment was applied to six of the lased spots on the treatment arm. One untouched spot on the contralateral arm was administered a thin layer of Diprolene (β-methasone), which is a strong steroid that can permeate the intact stratum corneum in an amount sufficient to cause measurable skin blanching. An occlusive patch, consisting of simple plastic wrap, was fixed with gauze and dermatological tape over all sites on both arms and left in place for two hours, after which the administered steroids were gently removed with cotton swabs. Colorimeter measurements were then taken over every unirradiated and irradiated spot at 2, 4, 8, 10, 12 and 26 hours post-irradiation, these results are shown in FIG. 38. Finally, the skin was clinically assessed for evidence of irritation at the 26 hour evaluation.

The results of the chromameter measurements show that some erythema (reddening) of the skin occurred, but because of the opposite-acting blanching permeating hydrocortisone, the reddening was less than that seen in the control spots which did not receive hydrocortisone. The Diprolene control proved the validity of the measurements and no problems were seen in the volunteers at the 26 hour evaluation, although in some of the cases the site of irradiation was apparent as a small red spot.

EXAMPLE 13

The radiant output of the Er:YAG laser is focussed and collimated with optics to produce a spot size at the surface of the skin of, for example, 5 mm. The skin of the patient, being the site of, or close to the site of, disease, is visually examined for anything that might affect the pharmacokinetics of the soon to be administered drug (e.g., significant erythema or a wide-spread loss of the integrity of the stratum corneum). This site, which is to be the site of irradiation, is gently cleansed to remove all debris and any extraneous compounds such as perfume or a buildup of body oils. A disposable tip attached to the laser pressed up to the skin prior to irradiation is used to contain any ablated biological debris, as well as to contain any errant radiant energy produced by the laser. A single laser pulse (approximately 350 µs long), with an energy of 950 mJ, is used to irradiate the spot. The result is a reduction or elimination of the barrier function of the stratum corneum. Subsequently, an amount of pharmaceutical, hydrocortisone for example, is spread over the irradiation site. The pharmaceutical may be in the form of an ointment so that it remains on the site of irradiation. Optionally, an occlusive patch is placed over the drug in order to keep it in place over the irradiation site.

While various applications of this invention have been shown and described, it should be apparent to those skilled in the art that many modifications of the described techniques are possible without departing from the inventive concepts herein.

We claim:
1. A method of measuring analyte concentrations in bodily fluids, comprising the steps of:
   a) focusing a laser beam with sufficient energy fluence to ablate the skin at least as deep as the stratum corneum, but not as deep as the capillary layer;

b) firing the laser to create a site of ablation, the site having a diameter of between 0.5 microns and 5.0 cm;

c) collecting a sample of interstitial fluid released by steps (a) and (b); and d) testing the interstitial fluid for analyte concentration.

2. The method of claim 1 wherein the laser beam has a wavelength of 0.2–10 microns.

3. The method of claim 1 wherein the laser beam has a wavelength of about 1.5–3.0 microns.

4. The method of claim 1 wherein the laser beam has a wavelength of about 2.94 microns.

5. The method of claim 1 wherein a laser selected from the group consisting of Er:YAG, pulsed $CO_2$, Ho:YAG, Er:YAP, Er/Cr:YSGG, Ho:YSGG, Er:GGSG, Er:YLF, Tm:YAG, Ho:YAG, Ho/Nd:Yalo$_3$, cobalt:MgF$_2$, HF chemical, DF chemical, carbon monoxide, deep UV lasers, and frequency tripled Nd:YAG lasers emits the laser beam.

6. The method of claim 1 wherein Er:YAG laser emits the laser beam.

7. The method of claim 1 wherein a modulated laser selected from the group consisting of continuous-wave $C)_2$, Nd:YAG, Thallium:YAG and diode lasers emits the laser beam.

8. The method of claim 1 including the step of focusing the laser beam at a site on the skin with a diameter of 0.1–5.0 mm.

9. The method of claim 1 wherein the energy fluence of the laser beam at the skin is 0.03–100,00 J/cm$^2$.

10. The method of claim 1 wherein the energy fluence of the laser beam at the skin is 0.03–9.6 J/cm$^2$.

11. The method of claim 1 wherein the laser creates multiple ablations to prepare the skin for diffusion of interstitial fluid.

12. The method of claim 1 wherein the laser creates multiple ablations to prepare the skin for pharmaceutical delivery.

13. The method of claim 1 further comprising a beam splitter positioned to create, simultaneously from the laser, multiple sites of ablation.

14. The method of claim 13 wherein the beam splitter is selected form a series of partially silvered mirrors, a series of dichroic mirrors, and a series of beam-splitting prisms.

15. The method of claim 1 further comprising an acousto-optic modulator outside the laser cavity wherein the modulator consecutively deflects the beam at different angles to create different sites of ablation on the skin.

16. The method of claim 1 wherein the analyte to be measured is selected from the group consisting of $Na^+$, $K^+$, $CA^{++}$, $Mg^{++}$, $Cl^-$, $HCO_3^-$, $HHCO_3$, phosphates, $S_4^{--}$, glucose, amino acid, cholesterol, phospholipids, neutral fat, $PO_2^{--}$, pH, organic acids or proteins.

17. The method of claim 1 including the step of determining the analyte concentration in blood by measuring the analyte concentration in the interstitial fluid.

18. The method of claim 1 including the step of collecting the interstitial fluid in a container positioned proximal to the ablation site and through which the laser beam passes.

19. The method of claim 18 wherein the analyte concentration is tested while the container unit is attached to the laser device.

20. The method of claim 1 further comprising the step of applying a therapeutically effective amount of a pharmaceutical composition at the site of ablation.

21. The method of claim 20 wherein the analyte concentration is used to determine the amount of pharmaceutical substance to be administered.

22. The method of claim 1 further comprising the step of applying a pressure gradient to the skin after formation of the site of abaltion to increase the diffusion rate of interstitial fluid.

23. The method of claim 1 further comprising the step of mechanically increasing the diffusion rate of interstitial fluid after formation of a site of ablation.

24. The method of claim 23 wherein sub-atmospheric pressure is applied at the ablation site to increase diffusion.

25. The method of claim 24 wherein the container unit is under sub-atmospheric pressure.

26. The method of claim 1 wherein the removal of bodily fluids is increased by applying a pressure gradient at the site of ablation.

* * * * *

UNITED STATES PATENT AND TRADEMARK OFFICE
CERTIFICATE OF CORRECTION

PATENT NO. : 6,387,059 B1  Page 1 of 1
DATED : May 14, 2002
INVENTOR(S) : Kevin S. Marchitto et al.

It is certified that error appears in the above-identified patent and that said Letters Patent is hereby corrected as shown below:

Column 7,
Line 11, "FRIR" should be -- FTIR --.

Column 8,
Line 6, "purse" should be -- pulse --.

Column 9,
Line 36, "Stem" should be -- Stern --.

Column 13,
Line 20, "(>approx. $10^8$ - $10^{10\ W/cm2}$)" should be -- (>approx. $10^8$ - $10^{10}$ W/cm$^2$) --.

Column 22,
Line 33, "holmiumlneodymium" should be -- holmium/neodymium --.

Column 24,
Line 14, "TRANSMEDICAT$^{TM}$" should be -- TRANSMEDICA$^{TM}$ --.

Signed and Sealed this

Twenty-fifth Day of February, 2003

JAMES E. ROGAN
*Director of the United States Patent and Trademark Office*